US010561437B2

(12) United States Patent
Radl et al.

(10) Patent No.: US 10,561,437 B2
(45) Date of Patent: Feb. 18, 2020

(54) SYSTEMS AND METHODS FOR REMOVING A TISSUE SPECIMEN OR ORGAN THROUGH A SMALL INCISION OR NATURAL OPENING IN A PATIENT

(71) Applicant: Boehringer Laboratories LLC, Phoenixville, PA (US)

(72) Inventors: Christopher L. Radl, Malvern, PA (US); Allison Lloyd Lehmann, Norristown, PA (US); Kevin P. Klocek, Wynnewood, PA (US); Trevor Smith, Round Lake Beach, IL (US)

(73) Assignee: Boehringer Laboratories LLC, Phoenixville, PA (US)

( * ) Notice: Subject to any disclaimer, the term of this patent is extended or adjusted under 35 U.S.C. 154(b) by 268 days.

(21) Appl. No.: 15/664,758

(22) Filed: Jul. 31, 2017

(65) Prior Publication Data

US 2017/0325834 A1 Nov. 16, 2017

Related U.S. Application Data

(63) Continuation-in-part of application No. 14/986,890, filed on Jan. 4, 2016, now Pat. No. 9,986,986.
(Continued)

(51) Int. Cl.
*A61B 17/3205* (2006.01)
*A61B 17/22* (2006.01)
(Continued)

(52) U.S. Cl.
CPC .. *A61B 17/32056* (2013.01); *A61B 17/00234* (2013.01); *A61B 17/22031* (2013.01);
(Continued)

(58) Field of Classification Search
CPC ........ A61B 17/00234; A61B 17/32056; A61B 2017/32006; A61B 2017/00287; A61B 2017/00862
See application file for complete search history.

(56) References Cited

U.S. PATENT DOCUMENTS 5,611,803 A 3/1997 Heaven et al.
5,647,372 A 7/1997 Tovey et al.
(Continued)

FOREIGN PATENT DOCUMENTS

EP 2540242 A1 1/2013
WO 2015164591 A1 10/2015

OTHER PUBLICATIONS

International Search Report for PCT/US2016/012169 dated Jun. 7, 2016.

*Primary Examiner* — Julian W Woo
(74) *Attorney, Agent, or Firm* — Caesar Rivise, PC

(57) ABSTRACT

Systems and methods for facilitating the removal of a tissue specimen from a patient are disclosed. The systems include a bag or pouch, a tissue cutter device, a support and a stabilizer. The tissue cutter device includes a passer, a wire, and a handle. The support is an elongated member. The passer is an elongated member configured to be coupled to the support and introduced as a temporary unit into the mouth of the bag or pouch in the patient's body holding the tissue specimen. The wire is attached to the passer. The temporary unit is configured to pass around the tissue specimen and out of the opening in the bag or pouch to carry the wire through that path so that a distal portion of the wire and a proximal portion of the wire are outside the patient's body. Those portions of the wire can be pulled to cut into the tissue specimen. The stabilizer holds the tissue specimen as the wire cuts into it. The bag or pouch includes direction-
(Continued)

bearing indicia to facilitate viewing of the methods from within the patient's body.

15 Claims, 17 Drawing Sheets

Related U.S. Application Data

(60) Provisional application No. 62/250,152, filed on Nov. 3, 2015, provisional application No. 62/159,520, filed on May 11, 2015, provisional application No. 62/117,056, filed on Feb. 17, 2015, provisional application No. 62/100,976, filed on Jan. 8, 2015.

(51) Int. Cl.
*A61B 17/00* (2006.01)
*A61B 17/3209* (2006.01)
*A61B 17/32* (2006.01)
*A61B 90/00* (2016.01)
*A61B 17/02* (2006.01)

(52) U.S. Cl.
CPC . *A61B 17/0206* (2013.01); *A61B 2017/00287* (2013.01); *A61B 2017/00349* (2013.01); *A61B 2017/00469* (2013.01); *A61B 2017/00862* (2013.01); *A61B 2017/32006* (2013.01); *A61B 2017/320024* (2013.01); *A61B 2017/32096* (2013.01); *A61B 2090/0811* (2016.02)

(56) References Cited

U.S. PATENT DOCUMENTS

| | | |
|---|---|---|
| 5,735,289 A | 4/1998 | Pfeffer et al. |
| 6,409,733 B1 | 6/2002 | Conlon et al. |
| 7,547,310 B2 | 6/2009 | Whitfield |
| 7,650,887 B2 | 1/2010 | Nguyen et al. |
| 7,670,346 B2 * | 3/2010 | Whitfield .......... A61B 17/00234 606/114 |
| 8,075,567 B2 * | 12/2011 | Taylor .............. A61B 17/00234 606/114 |
| 8,282,572 B2 | 10/2012 | Bilsbury |
| 8,409,112 B2 | 4/2013 | Wynne et al. |
| 8,486,087 B2 | 7/2013 | Fleming |
| 8,652,147 B2 | 2/2014 | Hart |
| 8,721,658 B2 | 5/2014 | Kahle et al. |
| 9,034,052 B2 | 5/2015 | Shimko et al. |
| 9,204,888 B2 * | 12/2015 | Cherry ................ A61B 17/221 |
| 9,468,452 B2 * | 10/2016 | Menn ............... A61B 17/00234 |
| 9,867,600 B2 * | 1/2018 | Parihar ........... A61B 17/00234 |
| 10,285,675 B2 * | 5/2019 | Gupta ............. A61B 17/00234 |
| 2007/0135781 A1 | 6/2007 | Hart |
| 2008/0221588 A1 | 9/2008 | Hollis et al. |
| 2009/0043315 A1 | 2/2009 | Moon |
| 2009/0192510 A1 | 7/2009 | Bahney |
| 2010/0219091 A1 | 9/2010 | Turner |
| 2010/0249646 A1 | 9/2010 | Wynne et al. |
| 2013/0131689 A1 | 5/2013 | Farascioni |
| 2013/0184536 A1 | 7/2013 | Shibley et al. |
| 2013/0274758 A1 | 10/2013 | Young et al. |
| 2014/0135788 A1 | 5/2014 | Collins |
| 2015/0320409 A1 | 11/2015 | Lehmann et al. |
| 2016/0262763 A1 | 9/2016 | Shankarsetty et al. |
| 2016/0302783 A1 | 10/2016 | Greenberg et al. |

* cited by examiner

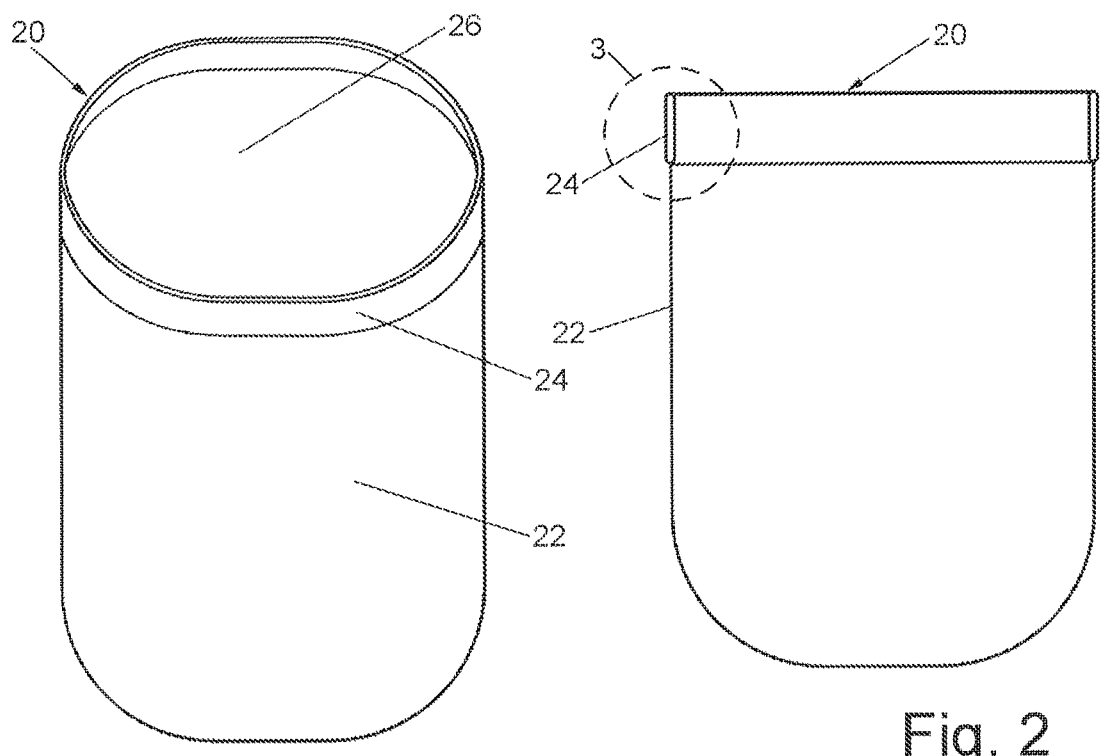
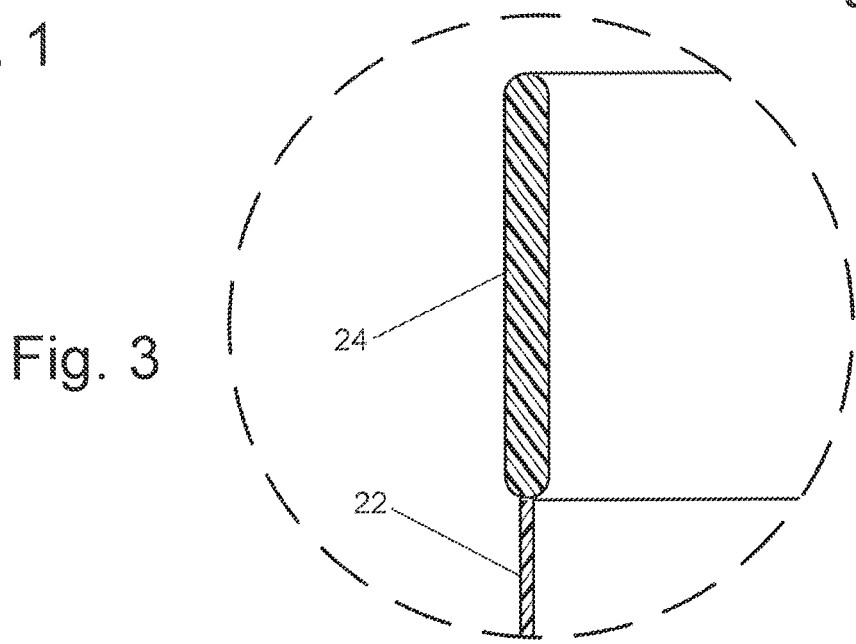
Fig. 1
Fig. 2
Fig. 3

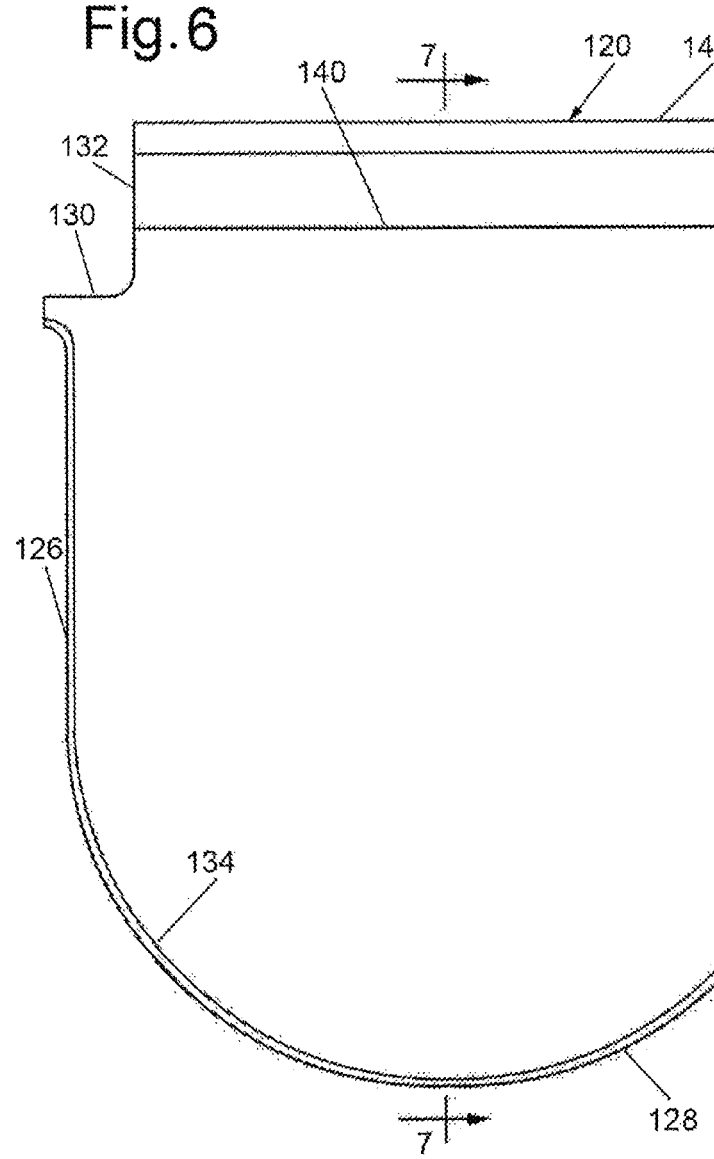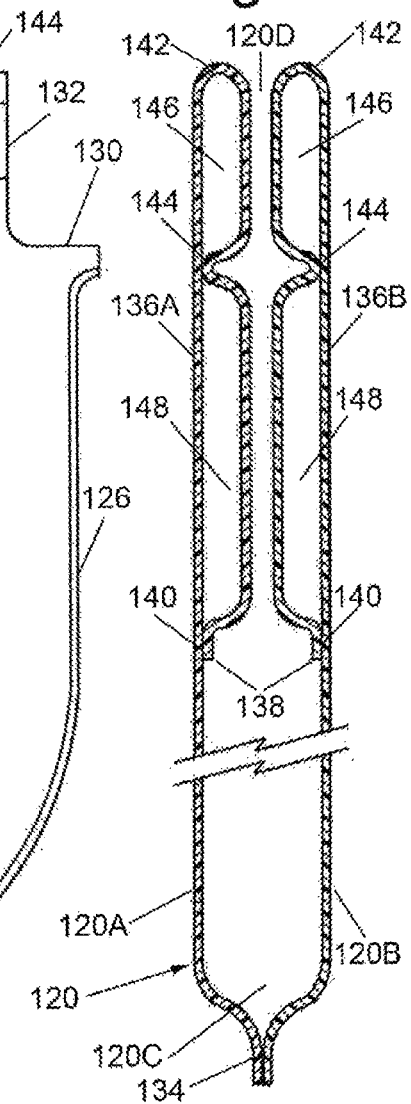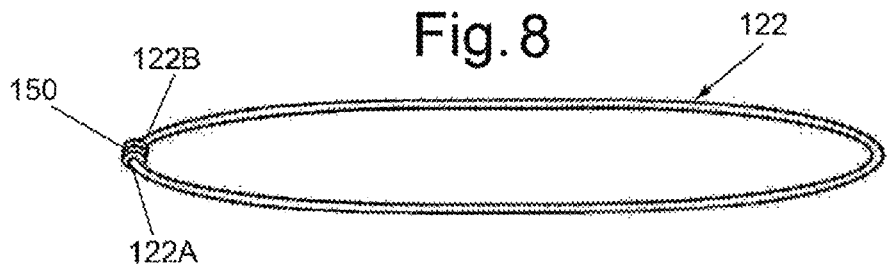

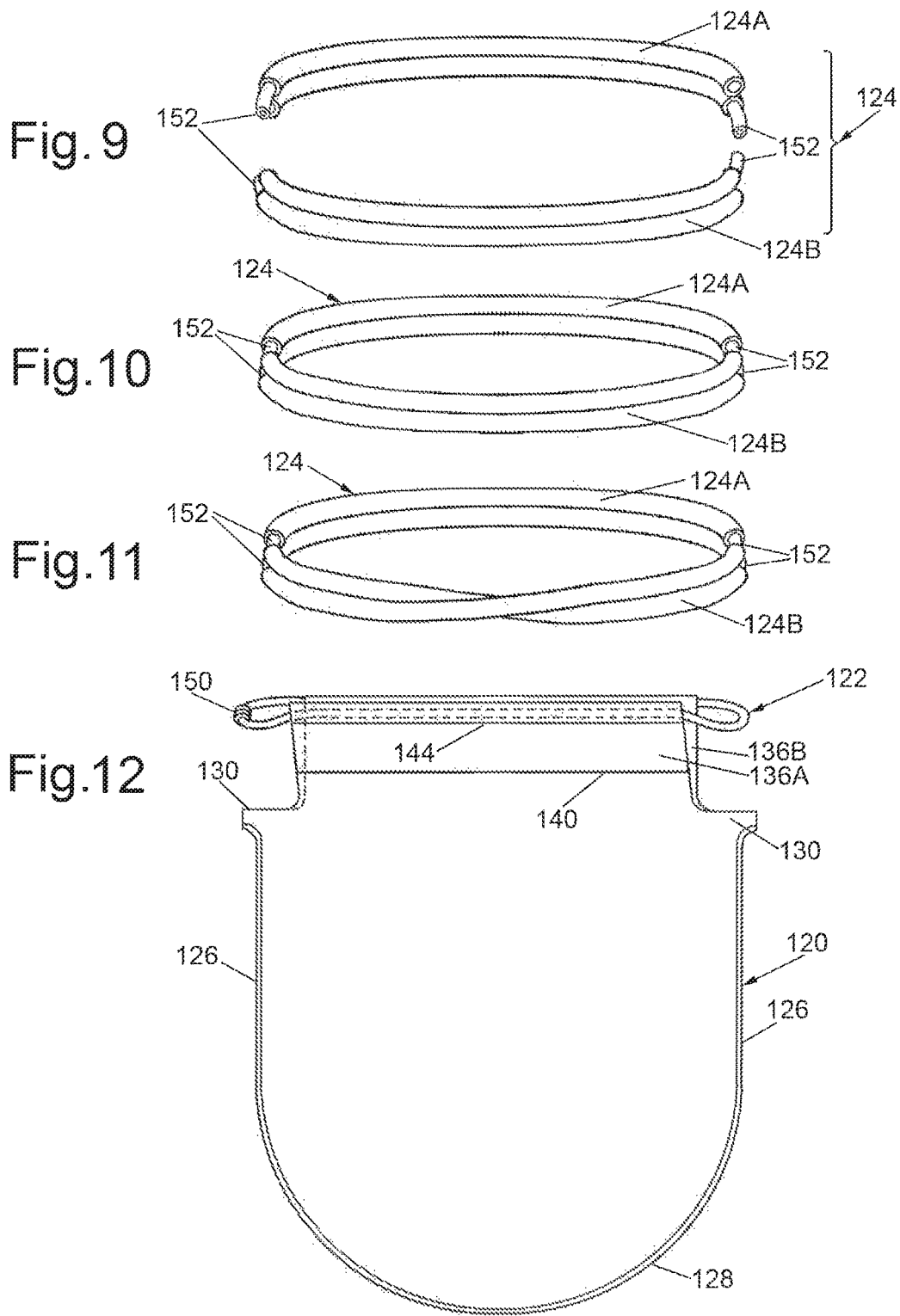

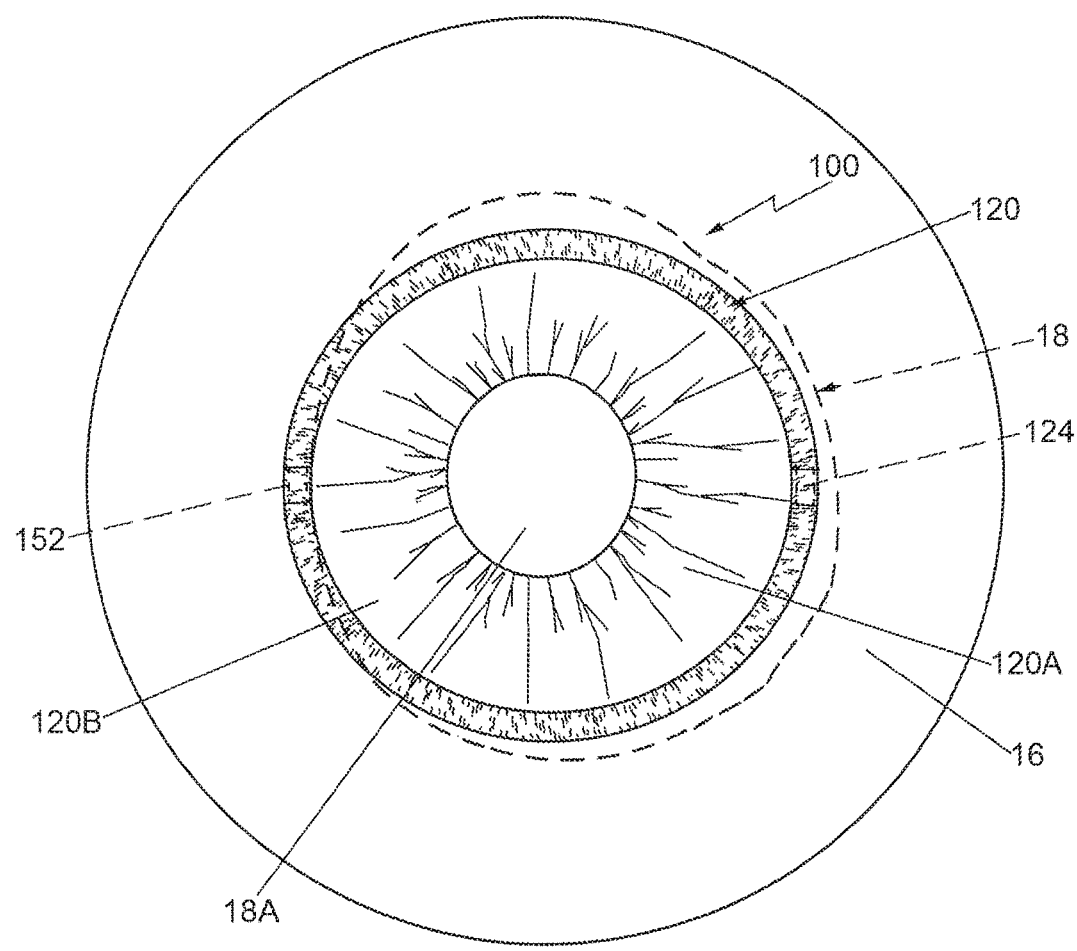

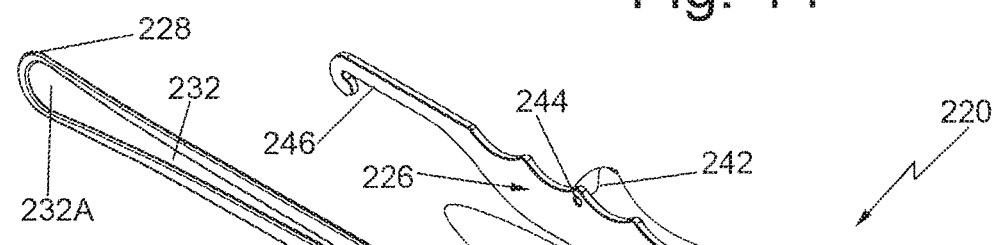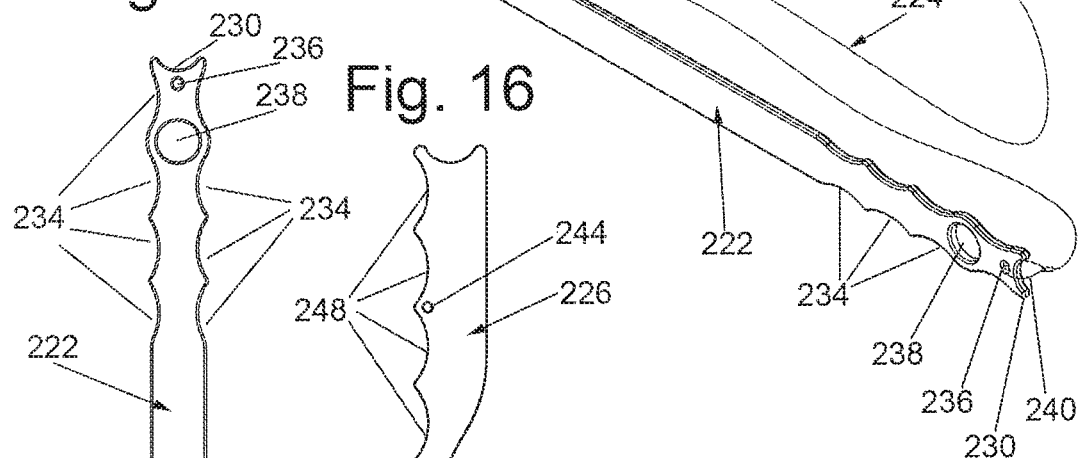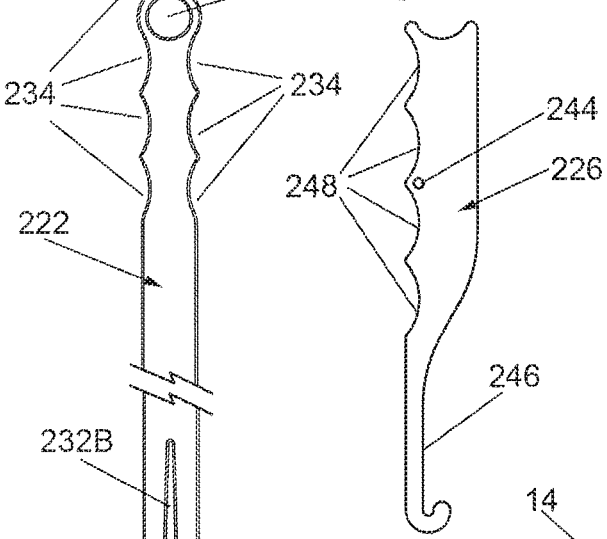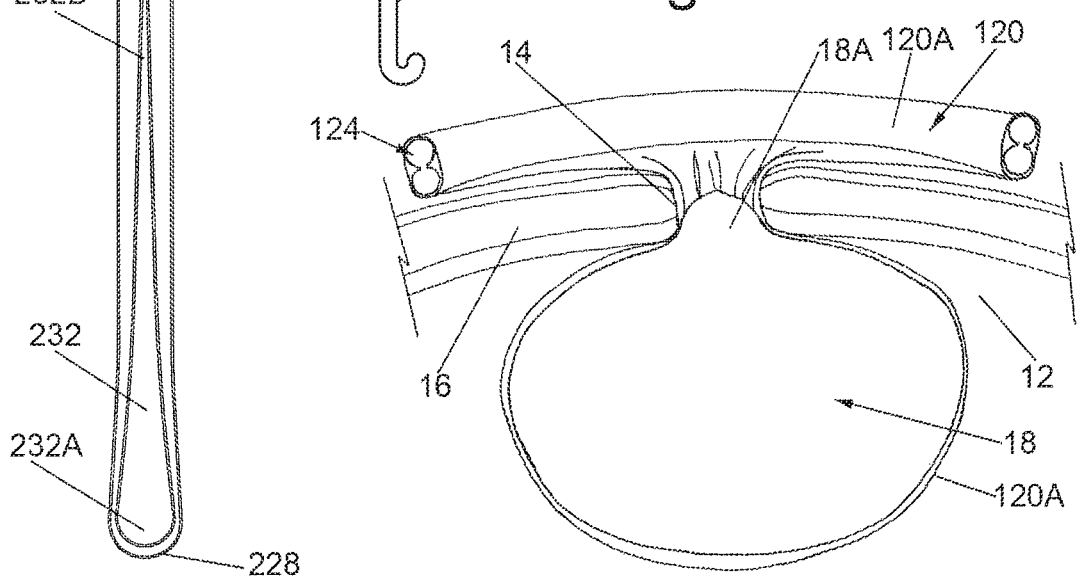

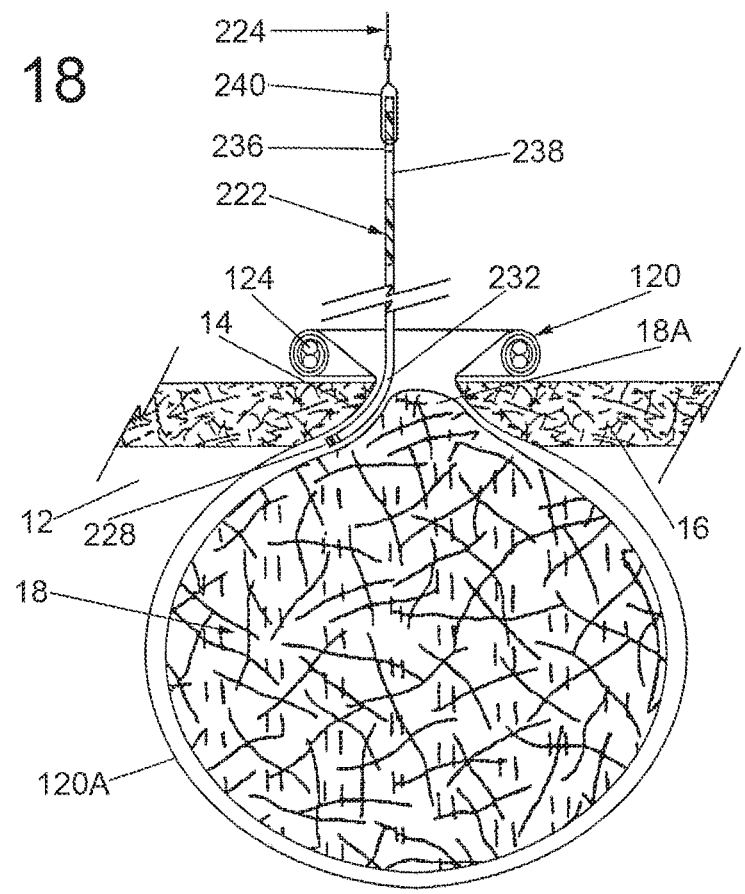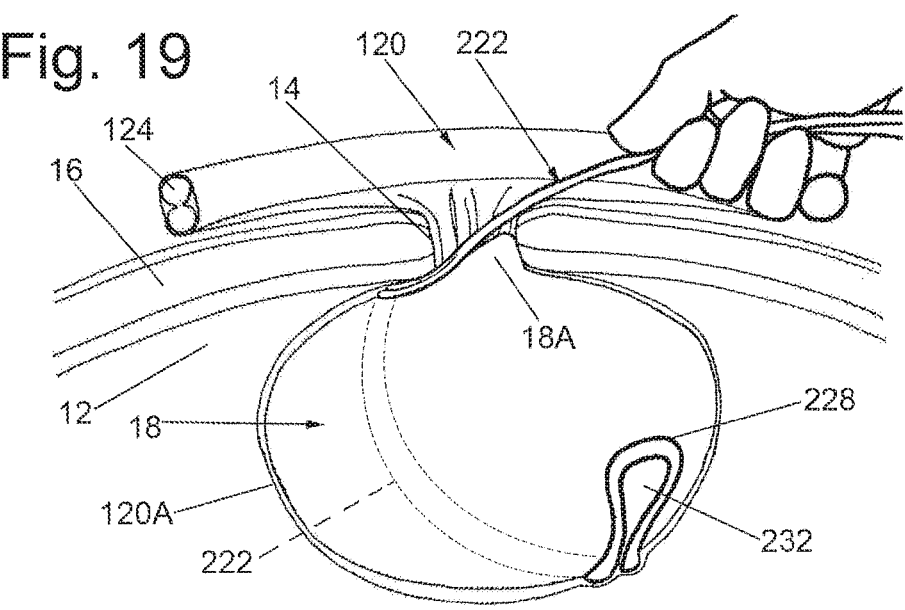

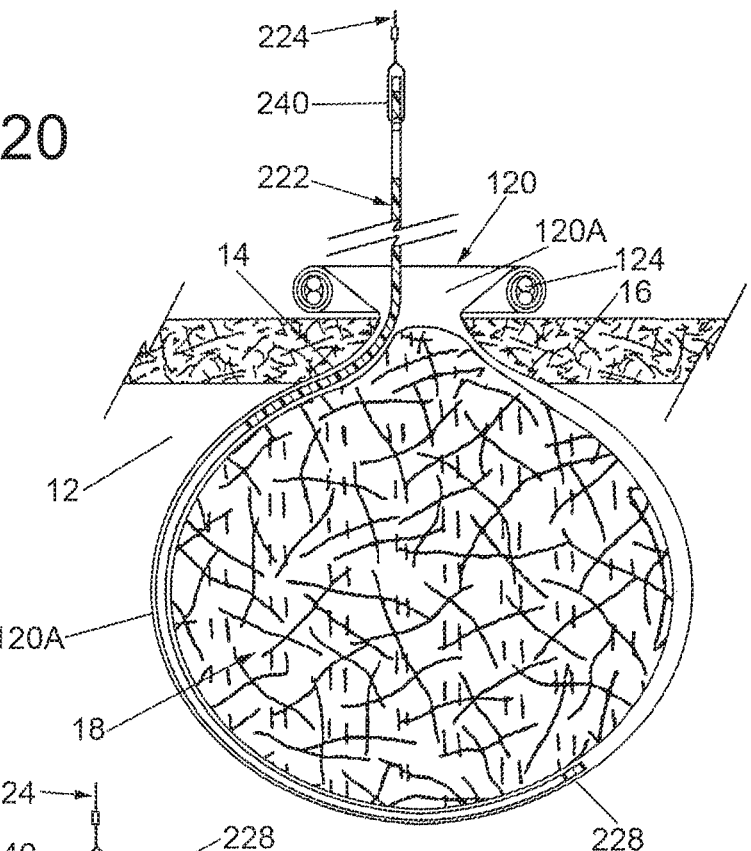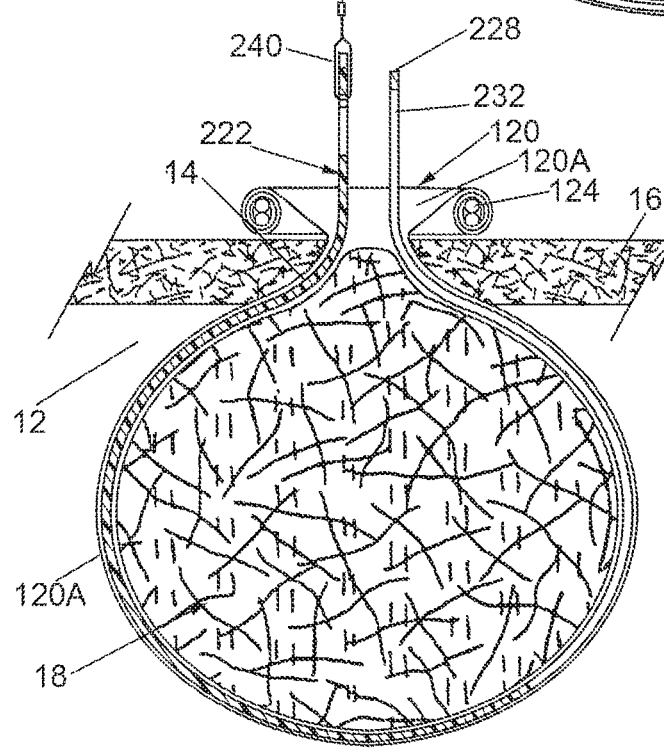

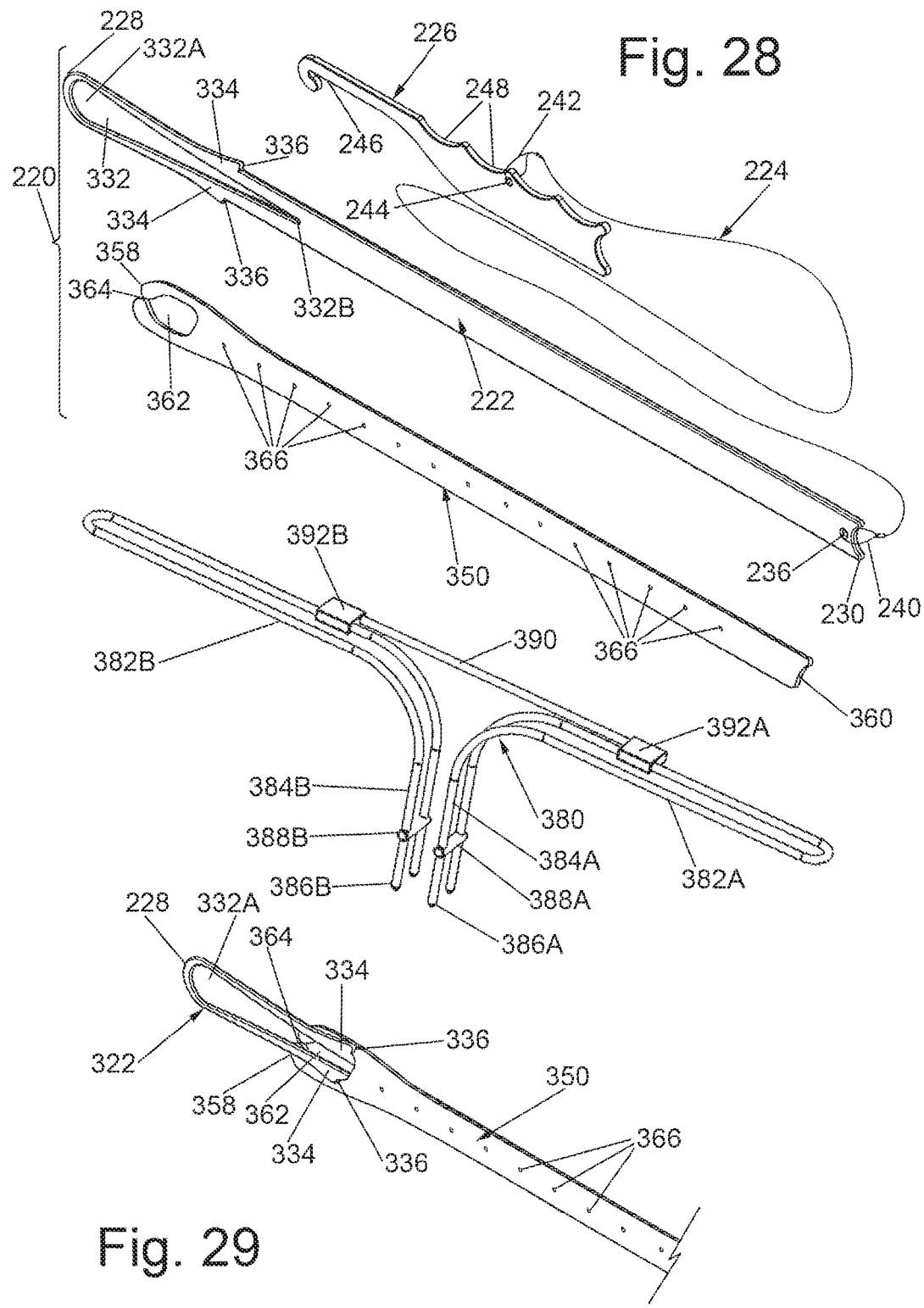

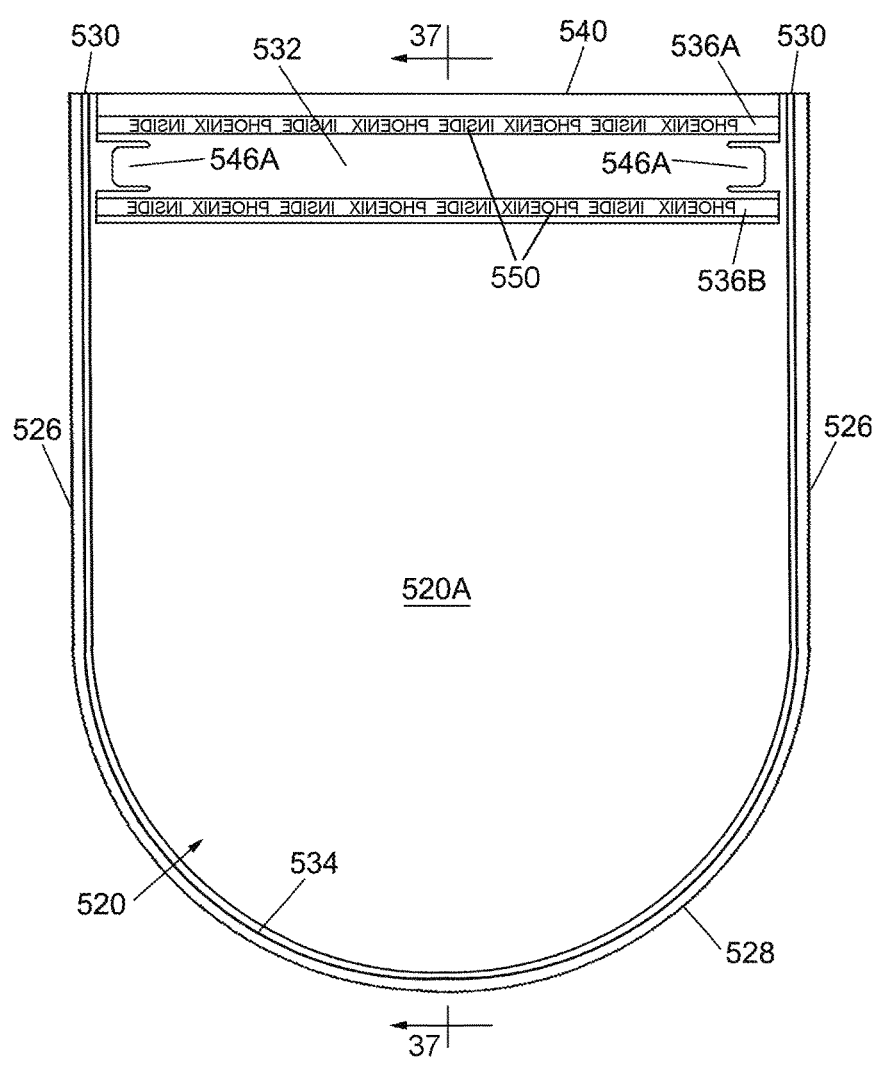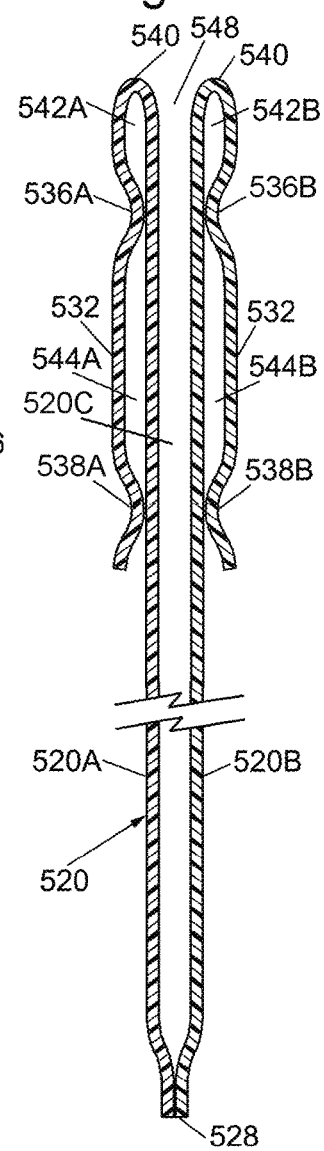

SYSTEMS AND METHODS FOR REMOVING A TISSUE SPECIMEN OR ORGAN THROUGH A SMALL INCISION OR NATURAL OPENING IN A PATIENT

CROSS-REFERENCE TO RELATED APPLICATIONS

This application constitutes a Continuation-In-Part of our prior application Ser. No. 14/986,890, filed on Jan. 4, 2016, entitled Systems for Removing a Tissue Specimen or Organ Through a Small Incision or Natural Opening in a Patient, now U.S. Pat. No. 9,986,986, which claims priority from U.S. Provisional application Ser. No. 62/100,976, entitled Collection Device For A Body Organ Or Tissue Specimen And Method Of Use, filed on Jan. 8, 2015; and Ser. No. 62/117,056, entitled Body Organ Or Tissue Specimen Collection Device And Method of Use, filed on Feb. 17, 2015; and Ser. No. 62/159,520, entitled Tissue Cutter Device And Method Of Use, filed on May 11, 2015; and Ser. No. 62/250,152, entitled Tissue Cutter Device And Method Of Use, filed on Nov. 3, 2015; all of which applications are assigned to the same assignee as this application and whose disclosures are incorporated by reference herein.

CROSS-REFERENCE TO RELATED APPLICATIONS

Statement Regarding Federally Sponsored Research or Development

Not Applicable

INCORPORATION-BY-REFERENCE OF MATERIAL SUBMITTED ON A COMPACT DISK

Not Applicable

FIELD OF THE INVENTION

The disclosed invention relates to medical devices and more particularly to systems and methods of use for removing an organ or tissue specimen through a small incision or natural opening in the body of a patient.

BACKGROUND OF THE INVENTION

More and more medical procedures for removing a targeted mass or specimen of tissue or an organ from the abdomen of a patient are accomplished laparoscopically to minimize scarring, infection, pain and other trauma. Typically the tissue specimen or organ is detached or freed from surrounding tissue using any conventional surgical techniques. Once that tissue specimen is free, it is ready for removal through the small incision into the abdomen (or via a suitable natural body orifice). If the targeted tissue specimen is too large to be removed as a whole unit through the incision or orifice, which quite commonly the case, the surgeon can resect it as necessary to reduce it in size or to a minimum of multiple pieces suitable for passing through the incision or orifice. Many of such procedures make use of a morcellator to reduce the size of the tissue specimen or organ.

As is known, morcellators are surgical instruments which typically take the form of a hollow cylinder that penetrates the abdominal wall and has a free distal end in the form of a high speed moving cutter or blade. Many morcellators include a central lumen or passageway through which a grasping instrument can be inserted to pull the tissue to be removed into a rotating cutter or blade to sever an extractable piece of that tissue, which is withdrawn out of the morcellator through its central passageway. While morcellators are effective for removing tissue from the body of the patient, the high-speed cutting action may free up some cells or other biological material, which can be dispersed within the peritoneal cavity. Thus, for example, if the tissue being removed is not known to be cancerous, but is in fact cancerous, there could be a release of cancer cells throughout the peritoneal cavity and from there elsewhere. Hence, it is possible for the process of morcellation to have an adverse effect on the patient.

In US2015/0320409, which is assigned to the same assignee as the subject invention, there is disclosed and claimed a system which addresses that problem by providing entrapment and collection systems and methods of entrapping and collecting biologic material produced during morcellation. Those systems include a collection bag which formed of a flexible sheet material having a hollow interior, a first mouth and a second mouth. The first mouth is openable to enable the biological structure to be disposed in the hollow interior and to enable a removal instrument, e.g., a morcellator, to be introduced therethrough to engage the biologic structure to effect a procedure on it. The second mouth enables a viewing instrument to be extended through it for visualizing the procedure and is closeable by a drawstring to entrap biologic material produced by the procedure after the removal instrument and viewing instrument have been removed, whereupon the collection bag may be withdrawn from the body of the patient.

Other systems have been disclosed in the patent literature to address the problem of containment of material produced during a morcellation procedure within the abdomen of a patent by means of a containment bag. For example, WO2015/164591 discloses a cut-resistant tissue guard removably insertable into a containment bag. The tissue specimen is isolated and contained within the containment bag and the guard is configured to protect the containment bag and surrounding tissue from incidental contact with sharp instrumentation used during morcellation and extraction of the tissue specimen. The guard is adjustable for easy insertion and removal and configured to securely anchor to the body opening. Protection-focused and containment-based systems for tissue removal are provided that enable minimally invasive procedures to be performed safely and efficiently. US2013/0184536 discloses a bag with one or more openings which is placed within a body cavity. Excised tissue is placed within the opening of a deflated bag. One or more opening in the bag are withdrawn outside the body cavity and the bag is inflated. Instruments, including laparoscopic visualization are placed within the inflated bag that remains within the body cavity. The tissue retained within the body cavity is morcellated/crushed/reduced and removed. The bag is deflated and removed with the residual tissue/blood/fluids inside. The tissue to be removed is retained in the bag which prevents potentially harmful material such as cancerous cells from being released in the body cavity.

The patent literature also includes various other relatively small, rolled-up or folded bags or pouches that are deployed and opened in the abdominal cavity where tissue is placed in them and then they are closed for retraction. See, for example, U.S. Pat. Nos. 8,652,147, 8,486,087, 8,409,112, 7,650,887, 6,409,733, 5,647,372, 2009/0043315, 2009/0192510 and 2008/0221588.

Notwithstanding the existence of the forgoing devices a need still exists for system and method for effecting the removal of a tissue specimen or organ through a small incision in the body of a patient making use of a collection bag and associated cutter components which are simple in construction, easy to use, which eliminate the need for power morcellators while minimizing the chances of dispersion of unwanted portions of the tissue specimen or organ, cells or other biological material into the peritoneum or other internal portion of the body in which the tissue specimen or organ is located. The subject invention addresses that need.

SUMMARY OF THE INVENTION

One aspect of this invention is a device for facilitating the removal of an organ or tissue specimen from the body of a patient through an opening in the patient's body. The organ or tissue specimen is located within an interior space in the patient adjacent the opening. The device comprises a bag or pouch, a support ring, and direction-bearing indicia. The bag or pouch has an interior cavity and is formed of a thin and flexible sidewall terminating in an open top forming a mouth in communication with the interior cavity. The support ring is located adjacent the mouth and configured to be collapsed by squeezing it to close the mouth. The flexible sidewall is configured to be collapsed to assume a compact state immediately adjacent the support ring to form a collapsed device configured to be inserted through the opening in the patient's body into the interior space. The direction-bearing indicia are configured when viewed by a viewing instrument from inside the interior cavity to appear in one condition and when viewed by a viewing instrument from outside the interior cavity to appear in another condition. The other condition is visually different than the one condition.

In accordance with one preferred aspect of the device of this invention the support ring is configured to automatically expands to a non-collapsed state opening the mouth when the bag or pouch is located within the interior space in the patient.

In accordance with another preferred aspect of the device of this invention the support ring comprises a ring-like member formed of nitinol wire and has a pair of ends, each of the ends is in the form of a connector. The connectors are configured to connect to one another to form the support ring.

In accordance with another preferred aspect of the device of this invention the device additionally comprises a section of heat shrinkable tubing configured for locking the connectors together once they have been connected.

In accordance with another preferred aspect of the device of this invention the device additionally comprises a split ring comprising at least one a split ring section. The bag or pouch is configured to mount the at least one split ring section adjacent the support ring. The at least one split ring section comprises a pair of ends that are configured to be connected together to form the split ring after the at least one split ring section is mounted to the panels. The split ring has sufficient strength to enable the panels to be rolled up about the support ring and the split ring.

In accordance with another preferred aspect of the device of this invention the bag or pouch comprises a pair of superimposed panels formed of a flexible material and which are connected together along portions of the periphery thereof to form the interior cavity, each of the panels including an outer surface and a top portion which is folded over the outer surface to from a top edge of the panel. The top portion is sealed to the outer surface of the panel by a first transverse seal line to form a first passageway or channel located between the top edge and the first transverse seal line. The top portion of the panel is sealed to the outer surface of the panel by a second transverse seal line to form a second passageway or channel located between the first transverse seal line and the second transverse seal line. The first passageway or channel is configured to receive a portion of the support ring therein. The second passageway or channel is configured to receive one of the split ring sections therein.

In accordance with another preferred aspect of the device of this invention the direction-bearing indicia are formed at least one of the first and second transverse seal lines.

In accordance with another preferred aspect of the device of this invention the first and second transverse seal lines are heat seal lines and wherein the indicia is embossed in the heat seal lines.

In accordance with another preferred aspect of the device of this invention the at least one split ring section comprises at least one connectors for connecting the ends of the at least one split ring section together.

In accordance with another preferred aspect of the device of this invention the at least one split ring section comprises plural lumens extending side-by-side along each other.

Another aspect of this invention is a method of removing a tissue specimen or organ from the body of a patient through an opening in the patient's body. The organ or tissue specimen is located within an interior space in the patient's body adjacent the opening. The method comprises providing a tissue specimen or organ isolating device comprising a flexible bag or pouch has an interior cavity, an open top forming a mouth in communication with the interior cavity, a collapsible support ring located adjacent the mouth, and direction-bearing indicia on the bag or pouch. The direction bearing indicia is configured when viewed by a viewing instrument from inside the interior cavity to appear in one condition and when viewed by a viewing instrument from outside the interior cavity to appear in another condition. The other condition is visually different than the one condition. The device is squeezed to collapse the support ring to close the mouth and thereby cause the device to be in a compact state. The collapsed device is inserted through the opening in the patient's body into the interior space. The mouth of the device is caused to open when the device is within the interior space. An excised tissue specimen or organ is caused to be located within the interior cavity. A viewing instrument is inserted into the interior space and caused to view the direction-bearing indicia to determine if the bag or pouch is being viewed by the instrument from inside the interior cavity of the bag or pouch or outside the bag or pouch.

In accordance with one preferred aspect of the method of this invention the collapsible support ring automatically opens the mouth of the device when the device is located in the interior space.

In accordance with another preferred aspect of the method of this invention the method additionally comprises collapsing the mouth of the device after the excised tissue specimen or organ is located in the interior cavity, withdrawing the collapsed mouth of the device out of the opening in the patient's body, causing the collapsed mouth of the device to open into a ring-like state, and rolling up the bag or pouch around the mouth to bring the excised tissue specimen or organ close to the opening in the patient's body where it can be seen from outside of the patient's body.

In accordance with another preferred aspect of the method of this invention the method additionally comprises removing the excised tissue specimen or organ from the patient's body through the mouth of the bag or pouch.

In accordance with another preferred aspect of the method of this invention the method additionally comprises removing the bag or pouch from the patient's body via the opening in the patient's body.

In accordance with another preferred aspect of the method of this invention the method additionally comprises resecting portions of the excised tissue specimen or organ from other portions thereof and removing the resected portions of the excised tissue specimen or organ from the patient's body via the opening in the patient's body.

In accordance with another preferred aspect of the method of this invention the method additionally comprises attaching a ring to the mouth of the device to cause the collapsed mouth to open into the ring-like state.

In accordance with another preferred aspect of the method of this invention the ring comprises at least one split ring section having a pair of ends connected together.

BRIEF DESCRIPTION OF THE DRAWING FIGURES

FIG. 1 is an isometric view of one exemplary tissue specimen or organ isolating device, e.g., a receptacle bag or pouch, constructed in accordance with this invention;

FIG. 2 is a vertical sectional view of the receptacle bag or pouch shown in FIG. 1;

FIG. 3 is an enlarged sectional view of a portion of the receptacle bag or pouch shown within the broken circle designated by the reference number 3 in FIG. 2;

FIG. 6 is a plan view of an exemplary embodiment of an alternative and more preferred bag or pouch forming one component of a tissue specimen or organ isolating device constructed in accordance with this invention, which device forms a portion of a system for facilitating the removal of an organ or tissue specimen from a patient's body;

FIG. 7 is an enlarged vertical sectional view taken along line 7-7 of FIG. 5;

FIG. 8 is an isometric view of a support ring forming another component of the tissue specimen or organ isolating device of this invention;

FIG. 9 is an isometric view of two split ring sections for forming a split ring, which constitutes another component of the tissue specimen or organ isolating device of this invention;

FIG. 10 is an isometric view of the two split ring sections of FIG. 9 shown connected together to form one exemplary embodiment of the split ring of this invention;

FIG. 11 is an isometric view similar to FIG. 10, but showing the two split ring sections of FIG. 9 shown connected together to form a more preferred exemplary embodiment of the split ring of this invention;

FIG. 12 is a plan view of the bag or pouch of FIG. 6 shown with the support ring of FIG. 8 mounted thereon, and with a portion of the mouth of the bag or pouch being shown folded down;

FIG. 13 is a top plan view showing the tissue specimen or organ isolating device of FIGS. 6-12 shown in position within the body of a patient, with the mouth portion of the bag or pouch extending out of an opening in the patient, and ready for use with other components of the system of this invention, such other components being a tissue cutter device, a passer and a stabilizer;

FIG. 14 is an isometric view of one exemplary embodiment of a tissue cutter device constructed in accordance with this invention;

FIG. 15 is a top plan view of the passer component of the tissue cutter device shown in FIG. 14;

FIG. 16 is a top plan view of the handle with hook component of the tissue cutter device shown in FIG. 14;

FIG. 17 is an isometric illustration, partially in section, showing a excised tissue specimen or organ disposed within the bag or pouch of the tissue specimen or organ isolating device like shown in FIG. 13 wherein that tissue specimen or organ is ready for sectioning by the tissue cutter device of FIG. 14;

FIG. 18 is a vertical sectional view of an insufflated abdomen of a patient with the pouch like shown in the illustration of FIG. 17 showing the introduction of the tissue cutter device of FIG. 14 into the pouch during an initial step in its use to effect the sectioning of the tissue specimen or organ;

FIG. 19 is an isometric illustration similar to FIG. 17, but showing a further step in the use of the tissue cutter shown in FIG. 14;

FIG. 20 is a vertical section view similar to FIG. 18, but showing the step in the use of the tissue cutter device of FIG. 14 in the step illustrated in FIG. 19;

FIG. 21 is a vertical sectional view similar to FIGS. 18 and 20, but showing a still further step in the use of the tissue cutter device of FIG. 14;

FIG. 28 is an isometric view, similar to FIG. 14, but showing of one exemplary embodiment of a more preferred tissue cutter system, constructed in accordance with this invention, and making use of a slightly modified tissue cutter device, a support component and a stabilizer component;

FIG. 29 is an isometric view of the distal end portions of the passer component of the tissue cutter device shown temporarily extended through a portion of the support component so that those temporarily combined two components are ready to be inserted into the body of the being for passage and transit about the specimen or organ;

Figure 5:
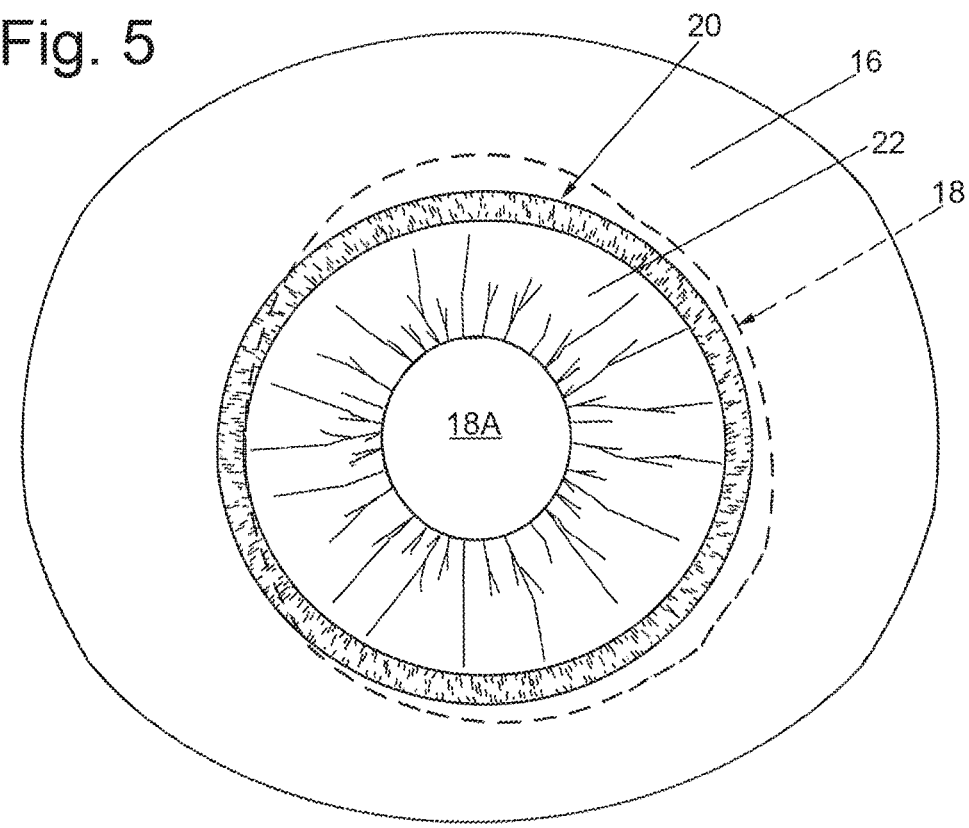
FIG. 5 is a slightly enlarged top plan view of the excised tissue specimen or organ illustrated in FIG. 4, wherein the tissue specimen or organ disposed within the bag or pouch of FIG. 1 ready for removal.
Figure 23:
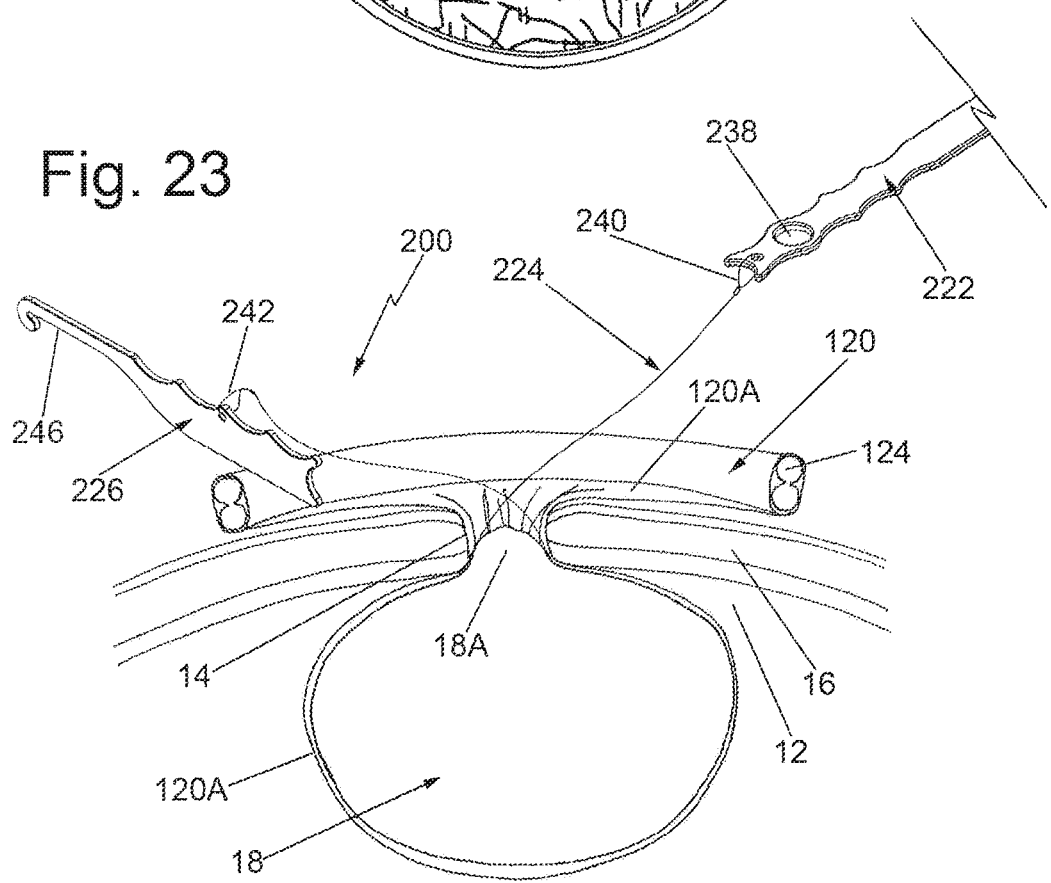
FIG. 23 is an isometric illustration, partially in section, similar to FIGS. 17 and 19, but showing a still further step in the use of the tissue cutter device of FIG. 14.
Figure 25:
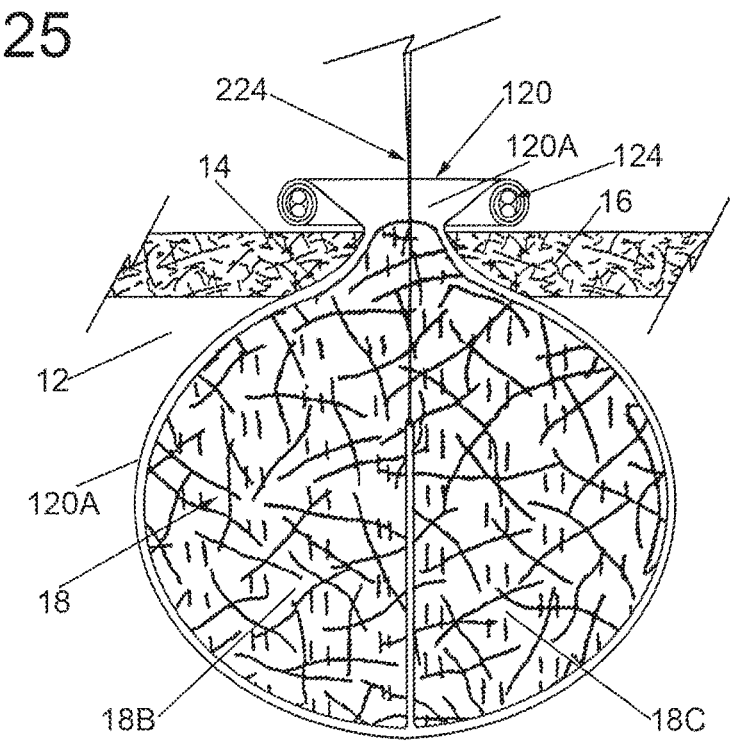
FIG. 25 is a vertical sectional view similar to FIGS. 18, 20, 21, 22, and 24, but showing a still further step in the use of the tissue cutter device of FIG. 14.
Figure 30:
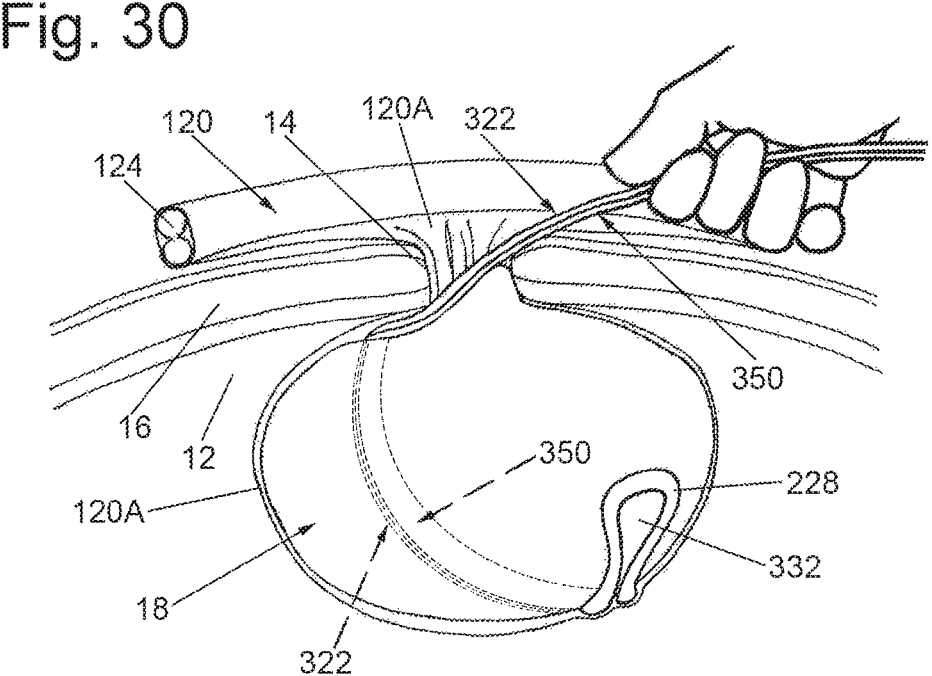
Figure 31:
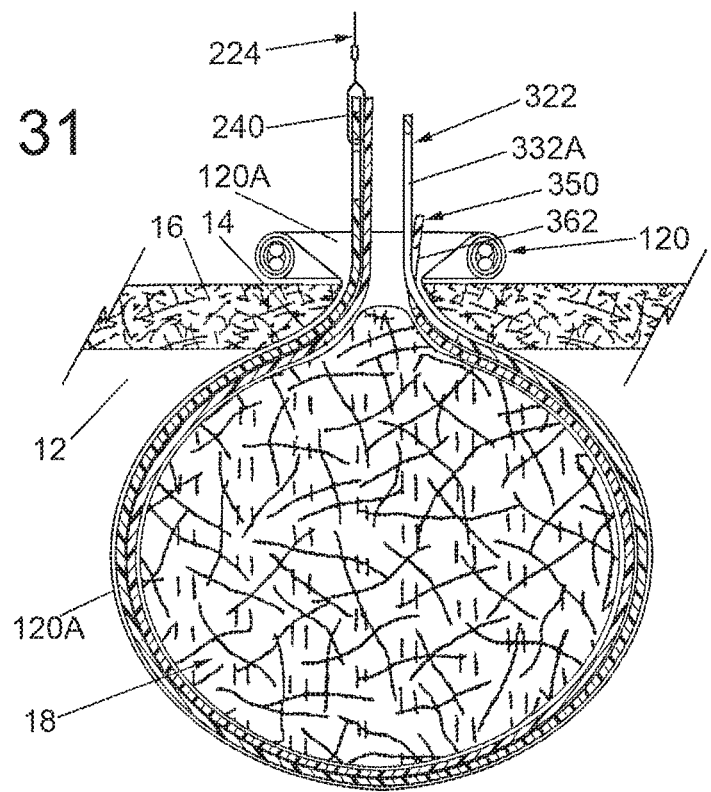
Figure 32:
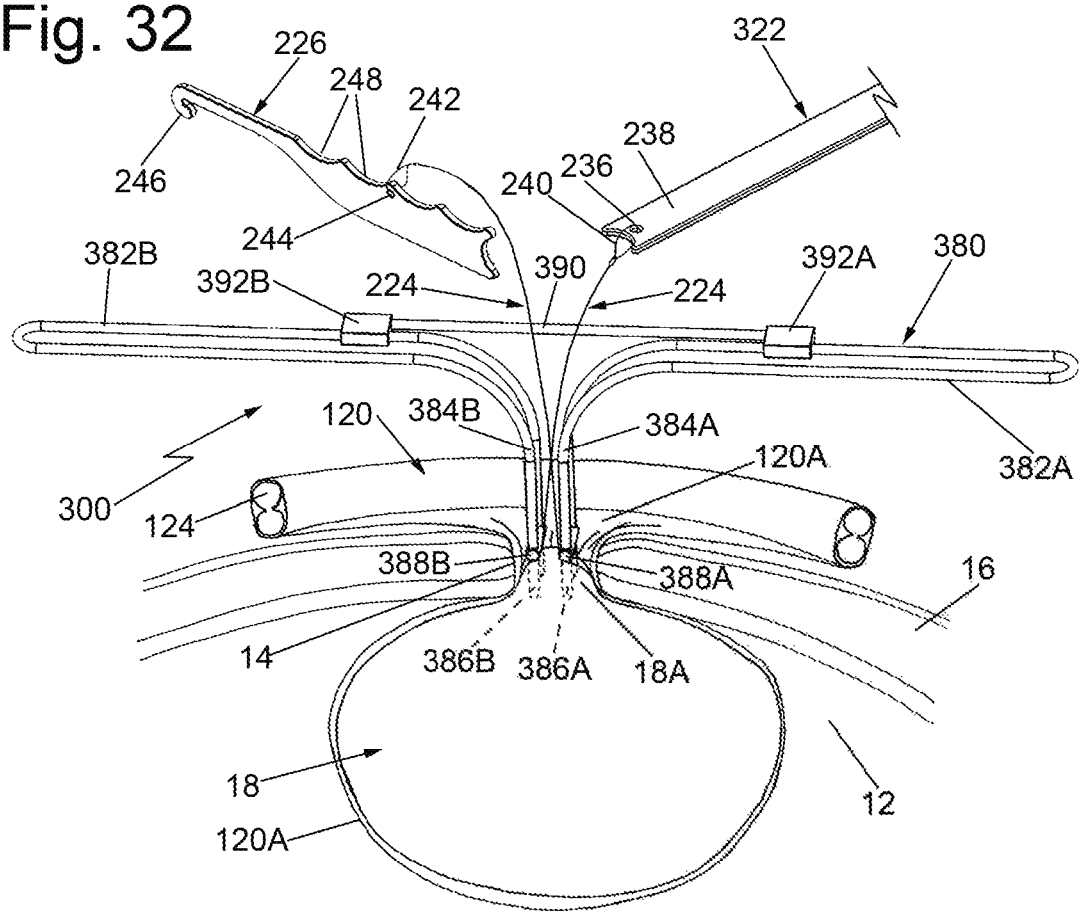
Figure 33:
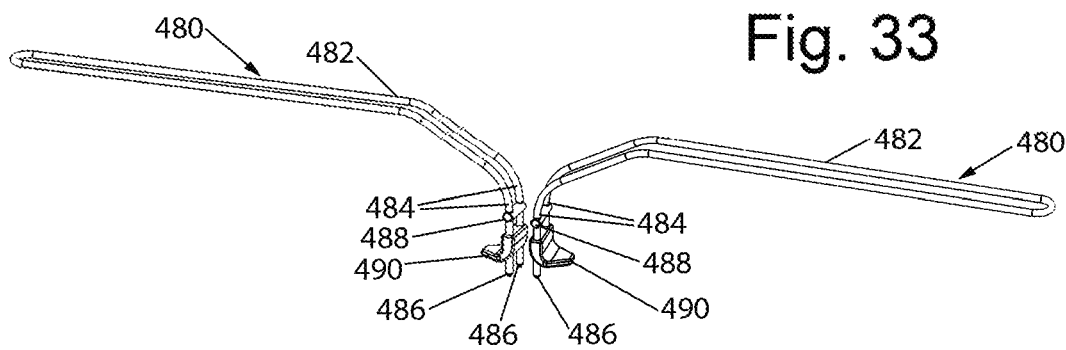
Figure 34:
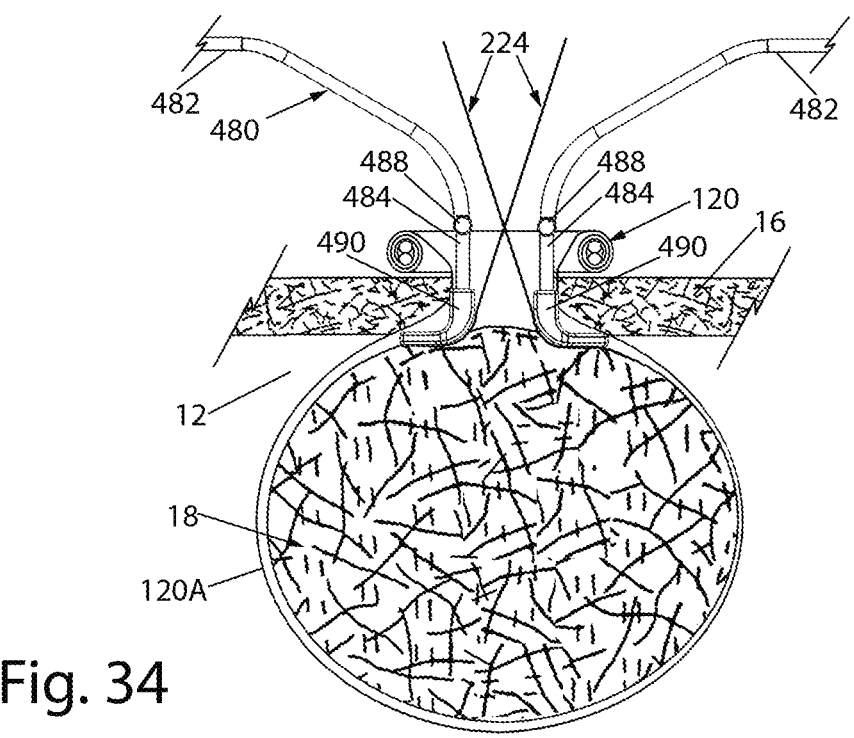
Figure 35:
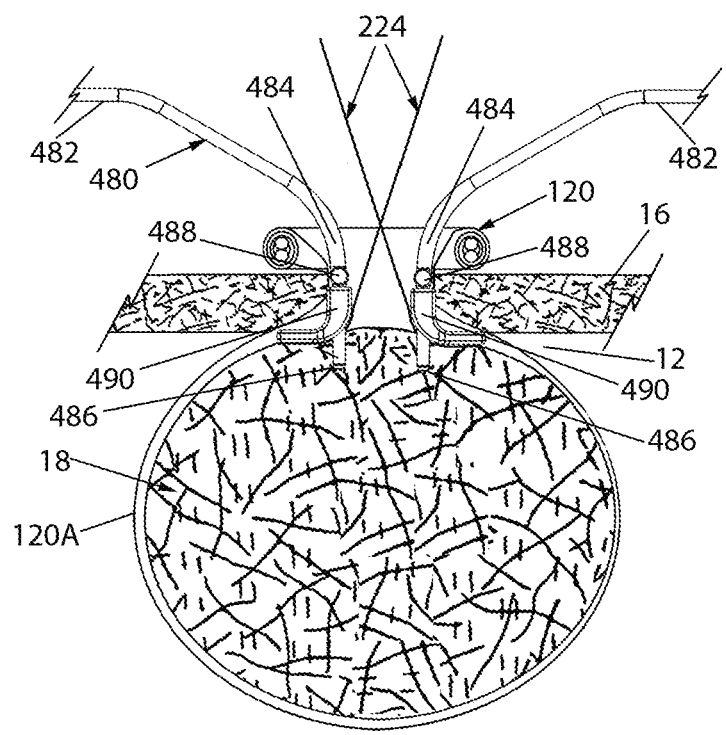
Figure 39:
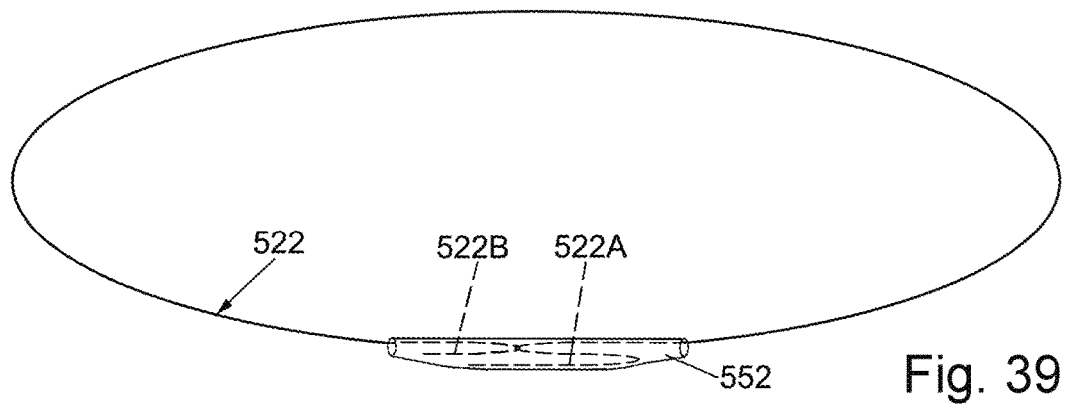
Figure 40:
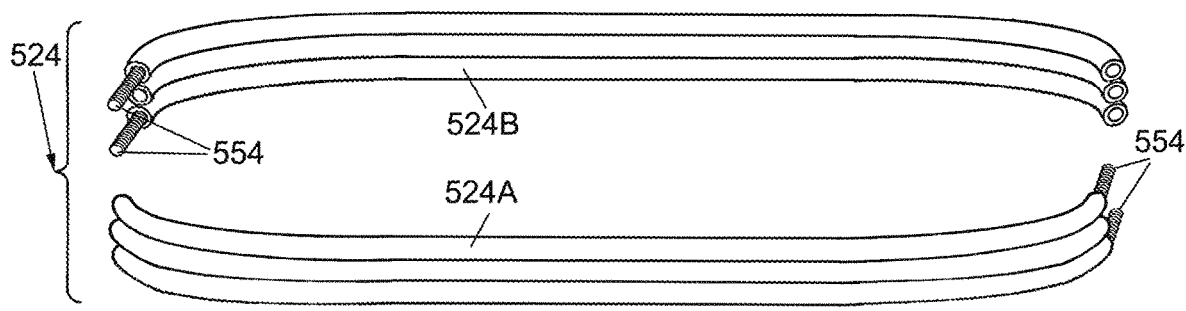
Figure 41:
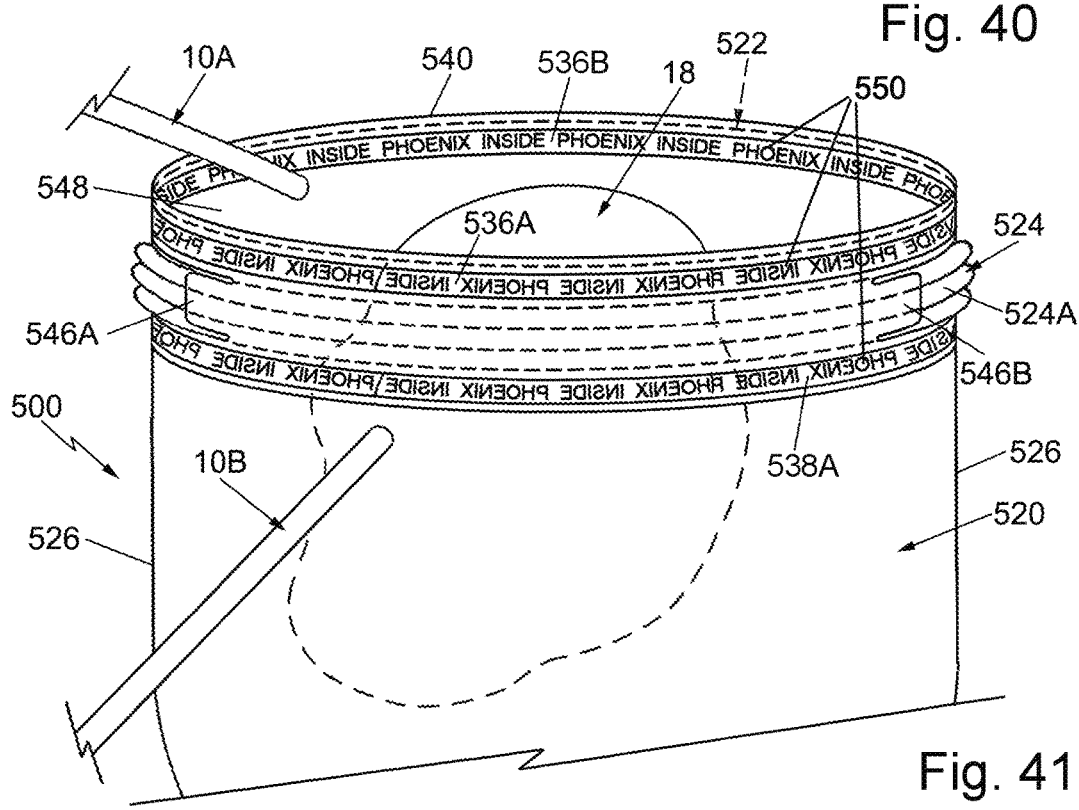

FIG. 30 is an isometric illustration, partially in section, similar to FIG. 19, but showing the excised tissue specimen or organ disposed within a tissue specimen or organ isolating device like illustrated in FIG. 6 in an insufflated abdomen of a patient wherein the temporarily combined passer and support component are shown during their transit about the specimen or organ during an intermediate step of the method of this invention;

FIG. 31 is a vertical sectional view, similar to FIG. 21, but showing the temporarily combined passer and support component after they have completed their passages about the specimen or organ within the pouch in the insufflated abdomen of a patient, whereupon the system is ready to have the support removed and to enable the passer and the cutter to thereafter be used to cut the specimen or organ into pieces for removal from the pouch;

FIG. 32 is an isometric illustration, similar to FIG. 23, but showing the use of the stabilizer component of the system of FIG. 28 in use to stabilize the specimen or organ during its sectioning;

FIG. 33 is an isometric view of a pair of alternative stabilizer components constructed in accordance with this invention;

FIG. 34 is an illustration, similar to FIG. 25 showing one step in the use of the stabilizer components shown in FIG. 33;

FIG. 35 is an illustration, similar to FIG. 34 but showing a later step in the use of the stabilizer components shown in FIG. 33;

FIG. 36 is a plan view of an exemplary embodiment of another alternative and most preferred embodiment of one component, i.e., a receptacle bag or pouch, of a tissue specimen or organ isolating device, which can be used alone or with the systems for facilitating the removal of an organ or tissue specimen from a patient's body constructed in accordance with this invention;

FIG. 37 is a greatly enlarged vertical sectional view of the bag or pouch taken along line 37-37 of FIG. 5;

FIG. 38 is an enlarged, exploded isometric view of the components making up a support ring, which forms another component for use with the bag or pouch of FIG. 36 to form a tissue specimen or organ isolating device constructed in accordance with this invention;

FIG. 39 is a reduced isometric view of the support ring of FIG. 38 in its assembled state;

FIG. 40 is an isometric view of two split ring sections for forming a split ring, which constitutes another component for use with the bag or pouch of FIG. 36 to form a tissue specimen or organ isolating device constructed in accordance with this invention; and FIG. 41 is an illustration showing the completed tissue specimen or organ isolating device composed of the components shown in FIGS. 36, 39 and 40, with the tissue specimen or organ isolating device being shown with a tissue specimen or organ located within the device and the device being viewed from various directions by laparoscopes.

DETAILED DESCRIPTION OF THE PREFERRED EMBODIMENTS

Referring now to the drawings wherein like characters refer to like parts there is shown in FIGS. 1-3 one exemplary embodiment of a tissue specimen or organ isolating device 20 constructed in accordance with this invention. The device 20 is in the form of a receptacle, e.g., a bag or pouch, or any other hollow flexible container. The device 20 is configured for facilitating the removal of a large organ or tissue specimen from within a space, e.g., the peritoneal cavity, in the body of a patient via an opening to that space. The opening may be an incision or natural body opening, such as the vagina. In accordance with one aspect of this invention the incision/opening is smaller than the organ/tissue specimen to be removed.

The bag or pouch 20 has a flexible sidewall 22. The sidewall terminates at its upper end in an open mouth 26. A semi-flexible ring-like member 24 is located at the mouth and is secured to the sidewall 22 thereat. The sidewall and the ring-like member can be formed of any suitable material(s). By way of example, in accordance with one exemplary embodiment of the invention the sidewall 22 of the device 20 is formed of 0.008" thick polyurethane film. The ring-like member 24 is also formed of polyurethane, but not a film, e.g., it is substantially thicker, e.g., 0.187" thick. The ring-like member, being semi-flexible, is collapsible so that diametrically opposed edges of it can be squeezed toward each to close the bag's mouth, whereupon the sidewall 22 can be collapsed, e.g., rolled up about the ring-like member, to form a collapsed device. With the device 20 in this state it is ready for easy introduction into the body of the patient through the incision or natural body opening. Once the device is inside the interior space in the patient and free of the incision/opening the device's mouth can spring back to reopen. Once that has been accomplished the excised organ or tissue specimen can be loaded into the device.

In particular, one exemplary use of the device 20 will now be described with respect to removal of a tissue specimen or organ from the peritoneal space in the body of a patient, wherein the tissue specimen or organ 18 (FIGS. 4 and 5) had previously been excised within the peritoneal space in an insufflated abdomen 12 (FIG. 5) via laparoscopic instruments (not shown). The opening through which the organ/specimen is to be accessed and removed constitutes an incision 14 (FIG. 4) in the abdominal wall 16. The device 20, is manipulated by squeezing its ring portion 24 (i.e., the device's mouth 26) closed and then collapsing, e.g., rolling the wall portion 22 about the closed mouth, so that one end of the collapsed (e.g., rolled up) device can be is inserted into the incision 14 to the peritoneal space in which the excised tissue specimen or organ to be removed is located. The device 20 is then pushed through the incision 14, whereupon when the mouth of the device 26 is within the space 12 and free of the incision 14 it will automatically open so that it is disposed adjacent the tissue specimen or organ 18 to be removed. A first grasper instrument (not shown) of any suitable type can then be inserted through the incision 14 to grasp a portion of the ring-like member 24 to pull the open mouth of the device to a desired position with respect to the organ to be removed. Another or second grasper instrument (not shown), can then be introduced through the incision so that its working end can be used to move the tissue specimen or organ into and through the mouth 26 of the device, while holding the device in place with the first grasper. Once the tissue specimen or organ is within the device 20, the first grasper instrument is used to grasp the ring-like member 24 of the device to start to pull the mouth of the device back out through the incision. Once an edge portion of the mouth of the device has been extended through the incision it can be grasped and pulled away from the body of the patient so that the entire periphery or edge of the device's mouth is outside the patient's body.

At that point, the tissue specimen or organ 18 and a portion of the device 20 containing it remain in the peritoneal space.

Figure 4:
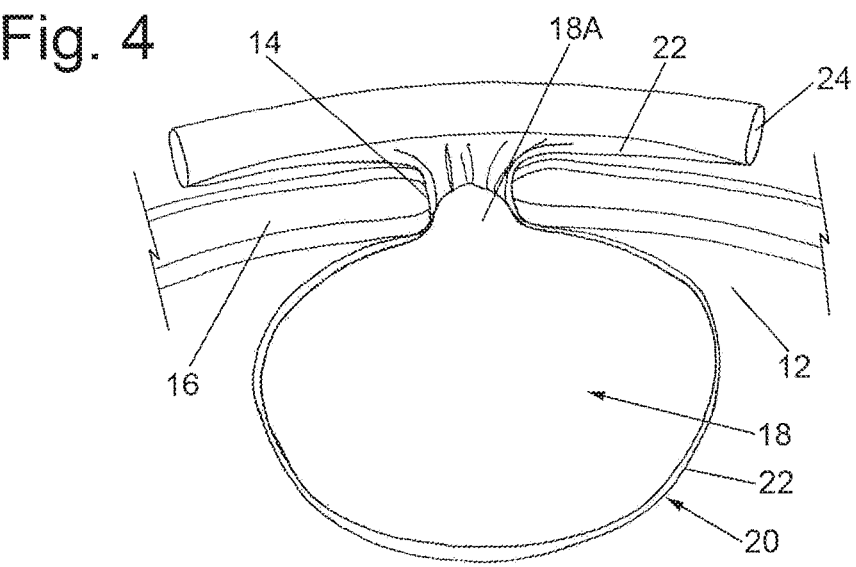
FIG. 4 is an isometric illustration, partially in section, showing a excised tissue specimen or organ disposed within the bag or pouch of FIG. 1 within the insufflated abdomen of a patient wherein that tissue specimen or organ is ready for removal, e.g., resection.

The ring-like member 24 of the device is then inverted or rolled up about itself multiple times. With each inversion of the ring-like member 24 a portion of the sidewall 22 is wrapped around the ring-like member. This serves the purposes of pulling the tissue specimen or organ 18 into the incision 14 and applying tension to the incision such that it is "retracted". Thus, a portion 18A of the tissue specimen or organ 18 will be located outside of the patient's body, such as shown in FIGS. 4 and 5. That extending portion 18A can be grasped, to pull it to a position where the surgeon can cut off pieces of the organ using a forceps and scalpel.

It should be pointed out at this juncture that the device 20 and method of use as described above are merely exemplary and thus other devices can be constructed in accordance with the teachings of this invention and other methods of removing an organ or tissue specimen from the body of a patient through an incision or natural body opening can be accomplished, as well. For example, there is shown in FIGS. 6-13 another and more preferred exemplary embodiment of a bag or pouch 120 forming one exemplary component of a tissue specimen or organ isolating device 100 (FIG. 13) constructed in accordance with this invention for facilitating the removal of a large organ or tissue specimen from within a space, e.g., the peritoneal cavity, in the body of a patient via an opening to that space. As mentioned previously the opening may be an incision or natural body opening, such as the vagina. In accordance with one aspect of this invention the incision/opening may be smaller than the organ/tissue specimen to be removed. The device 100 basically comprises the bag or pouch 120 (FIG. 6), a support ring 122 (FIG. 8) and a split ring 124 (FIGS. 9-11). The split ring 124 is made up of a plurality of split ring sections which are arranged to be connected together. In the exemplary embodiment shown the split ring is composed of two sections 124A and 124B, shown in FIG. 9-11. The details of the support ring 122 and the split ring 124 will be described later.

As can be seen in FIGS. 6, 7 and 12 the bag or pouch 120 is in the form of a hollow structure formed by a pair of panels 120A and 120B. Each panel is formed of a sheet or web of a thin flexible material, e.g., polyurethane film that is 0.008 inches thick. Both panels are of the same size and shape as the other panel and the panels are superimposed on each other. In the exemplary embodiment shown each panel has a pair of long, linear side edges 126, an arcuate, e.g., semi-circular bottom edge 128, a pair of ear portions 130 projecting outward from the top ends of the side edges 126, a pair of short, linear 132 side edges located above the ear portions 130. The panels 120A and 120B are connected together along a heat seal line 134 extending close and parallel to the adjacent peripheral edges of the panels form a hollow interior cavity 120C (FIG. 7) within the bag or pouch. The two ends of the seal line 134 terminate at respective ear portions 130. The short side edge portions 132 of the panels 120A and 120B which are located above the ear portions, are not sealed together and form a pair of flaps 136A (FIG. 6) and 136B (FIG. 12). In an alternate configuration the ear portions 130 are omitted and the heat seal line is extended all the way to the top edge of the bag 142.

As best seen in FIG. 7, the free end or edge 138 of each flap is folded over and sealed to the inner surface of the panel from it projects by a linear transverse seal line 140. The point at which each flap is folded forms the top edge 142 of the bag or pouch. Another linear transverse seal line 144 seals each of the folded over portions of the flaps close to the top of the bag or pouch. The two transverse seal lines 140 and 144 form a first passageway or channel 146 in each flap adjacent the top of the bag or pouch and a second, and wider width passageway or channel 148 in each flap below the first passageway or channel 146. Inasmuch as the flaps are not connected together, they form an open mouth 120D of the bag or pouch 120. The mouth 120D is in communication with the hollow interior cavity 20C.

The support ring 122 is best seen in FIG. 8 and basically comprises an elongated flexible and somewhat resilient member having a pair of ends 122A and 122B. One preferred exemplary embodiment of the support ring is formed of polyurethane tubing having an outer diameter of 0.125 inches. The flexible tube making up the support ring is extended through the channels 146 in the two flaps 136A and 136B, with the ends 122A and 122B of the tube being fixedly secured together by a barbed tube connector 150 to form a ring-like structure surrounding the mouth 120D of the bag or pouch as shown in FIG. 12. Being flexible and somewhat resilient, the support ring 122 is configured to be collapsed or flattened to facilitate the introduction of the pouch into the patient, as will be described later. The support ring can also be constructed from a section of nitinol wire with a connector, e.g., a hook, formed at each end. The two hooks are interlocked and a portion of heat shrink tubing is secured over the hooks to ensure that the hooks remain interlocked.

Turning now to FIGS. 9-11, the details of the split ring 124 will now be described. The split ring 124 is made up of plural elongated flexible split ring sections which are arranged to be extended through the channels 148 in the flaps 136A and 136B and thereafter connected together to form the split ring 124 and to connect that split ring to the bag or pouch 120. The assembly of the split ring and its connection to the bag or pouch is accomplished during the process of using the bag or pouch and will be described later. Suffice for now to state that after the tissue specimen or organ has been disposed within the bag or pouch within the patient's insufflated peritoneal space, the mouth 120D of the bag or pouch is withdrawn through the incision 14 into the peritoneal space and the split ring sections 124A and 124B are extended through the channels 148 in the flaps 136A and 136B so that they can be connected together. Once that has been accomplished the portion of the bag or pouch that is now located outside the patient's abdomen can be rolled up about the split ring and the support ring to bring the portion of the bag or pouch still within the patient's peritoneal space closer to the incision so that the tissue specimen or organ located therein can be removed.

In the exemplary embodiment shown in FIGS. 9-11, the split ring is made up of two split ring sections 124A and 124B. Each section is identical in construction and comprises a dual lumen tube, e.g., polyurethane tubing with a durometer in the 80-90 Shore A range, with each lumen of the tube having an inside diameter of 0.25 inches and an outside diameter of 0.375 inches. In order to effect the connection of the two split ring sections 124A and 124B together to form the split ring four connectors 152 are provided. The two split ring sections 124A and 124B can be connected various ways. For example, they can be connected as shown in FIG. 8 wherein the dual lumens of two sections are oriented parallel to each other so both ends of one lumen are located above both ends of the other lumen. In the embodiment of FIG. 11, the dual lumens of one section are twisted 180 degrees. In particular, the lumens of section 124B are twisted 180 degrees so that the end of the lumen at the left side of that section that is uppermost is lowermost at the right side of that section and the end of the lumen of that section that is lowermost at the left side is uppermost at the right side. It has been found that twisting the lumens in that manner facilitates the rolling up of the pouch by requiring less force to flip or rotate the split ring during the rolling-up process.

As mentioned above, another aspect of this invention constitutes a method of using a device 100 like that described above to remove an organ or tissue specimen from the peritoneal space in the body of a patient, after the organ or tissue specimen has been excised within the peritoneal space via laparoscopic instruments so that it is free within the peritoneal space. To that end the bag or pouch 120 is folded into a compact configuration for introduction through that incision 14 into the insufflated peritoneal space 12 located there-below. In particular, the lower portion of the bag or pouch 120 is folded up or rolled towards the support ring 122 at the opening or mouth of the bag or pouch to collapse the bag or pouch into a compact or narrow structure suitable for introduction through the incision into the peritoneal space.

Once the bag or pouch and the support ring secured thereto have been collapsed, with the mouth of the bag or pouch directed upward, the collapsed bag or pouch and its support ring can be inserted through the incision 14 into the patient's peritoneal space. To that end, the trocar that had been extended through the incision is removed, and the collapsed bag or pouch and its support ring is extended through the incision so that the bag or pouch and its support ring are fully within the peritoneal space. Alternatively, the bag or pouch and it support ring can be inserted into the peritoneal space through the trocar without removal of the trocar from the patient. This may be done in order to better maintain pneumoperitoneum during insertion. In either case, inasmuch as the support ring is somewhat resilient it will tend to spring back somewhat, thereby opening the mouth of the bag or pouch when it is free of the incision or trocar, as the case may be.

Once the bag or pouch 120 is in place within the peritoneal space 12, the trocar (not shown) can be reinserted into the peritoneal space via the incision. A grasper instrument of any suitable type (not shown) can then be inserted through the trocar extending through the incision through which the bag or pouch was inserted and additional graspers (not shown) can be extended through other trocars (not shown) into the peritoneal space. These graspers can be used to grasp the bag or pouch 120 to ensure that the mouth of the bag or pouch is open and to pull the open mouth of the bag or pouch to a desired position with respect to the excised organ or specimen 18 to be removed. Thus, for example, the grasper that is extended through trocar in the incision into which the bag pouch was inserted can be used to hold the bag or pouch with the open mouth at a desired position and a second grasper extending through another trocar can be used to move the excised tissue specimen or organ into and through the mouth of the bag or pouch, while holding the bag or pouch in place with the first grasper.

Once the tissue specimen or organ 18 is within the bag or pouch 120, the incision 14 into which the bag or pouch was inserted can be enlarged by use of a scalpel if necessary. The trocar extending through the incision into which the bag or pouch had been inserted can then be withdrawn along with the grasper extending therethrough to pull a portion of the mouth of the bag or pouch through the incision so that it is located outside of the patient's abdomen, whereupon the mouth of the bag or pouch 120 is "externalized". Once the mouth of the bag or pouch is fully outside the incision, the resilient nature of the support ring 122 will cause the mouth of the bag or pouch 120 to spring open. At that point the bag or pouch is ready to have the spit ring 124 mounted thereon. To that end, one end of the split ring section 124A is inserted into one end of the channel 148 of the flap 136A. The split ring is slid down that channel until the end of the split ring exits the opposite end of that channel. The other split ring 124B is inserted into one end of the channel 148 in the other flap 136B and extended therethrough until it exits the opposite end of that channel. The two ends of the spit ring sections 124A and 124B are then connected together using the connectors 152.

Once the spit ring 124 has been assembled, i.e., connected together, it is ready to have the bag or pouch 120 rolled up about it and the support ring 122. To that end, the split ring 124 is flipped or rotated inward, thus rolling it up. That rolling or flipping action is repeated, with each inversion of the split ring causing a portion of the bag or pouch to be wrapped around it and the support ring. This serves the purposes of pulling the tissue specimen or organ 18 into the incision 14 and applying tension to the incision such that a portion of the organ or tissue specimen will be located within the rolled-up portion of the pouch outside of the patient's body, as shown in FIG. 13. At that point the surgeon can cut off pieces of the tissue specimen or organ using forceps and scalpel. Once the organ or specimen has been cut away and removed, the extending portion of the bag or pouch 120 can be grasped to remove it from the incision 14, thereby carrying with it any residual portions of the organ or tissue specimen, e.g., cells, etc. that had not been removed. After the bag or pouch 120 has been removed from the patient, the incision 14 is ready for closure.

Referring now to FIG. 14 one exemplary embodiment of a tissue cutter device 220 constructed in accordance with this invention is shown. The tissue cutter device 220 forms one portion of a system 200 (FIG. 23) of this invention for effecting the removal of a tissue specimen or organ from the body of a patient. The tissue cutter device 220 is particularly suitable if the tissue specimen or organ is large relative to the size of the incision and if resection of that tissue specimen or organ by means of a scalpel and forceps would be difficult or otherwise undesirable. The tissue cutter device 220 is configured to be used with any bag or pouch that enables a tissue specimen or organ located therein to be brought to an internal position within the patient's body contiguous with a small opening in the patient's body so that the tissue specimen or organ can be removed through that small opening. It is preferred, however, that the cutter device 220 of the subject invention be used with a pouch or bag constructed in accordance with the subject invention, e.g., bag or pouch 120. Thus, the tissue cutter device 220 is shown in the figures of this application used with the pouch or bag 120. The tissue cutter device 220 when used in accordance with a method aspect of this invention facilitates the piece-meal cutting of a large tissue specimen or organ held within the bag or pouch so that it can be effectively removed piece-meal through the small opening, while the bag or pouch contains and holds any tissue fragments, blood, fluids or cells (hereinafter referred to as "tissue remnants") that may become separated from the tissue specimen or organ during the cutting operation to prevent such tissue remnants from gaining access into the patient's body.

As best seen in FIGS. 16-18, the tissue cutter device 220 basically comprises three components, namely, a passer 222, a wire 224 and a handle 226. The passer basically comprises a long flexible member having a distal end 228 and a proximal end 230. The passer is formed of any suitable material, such as high density polyethylene or any other suitable plastic. The passer is flexible to facilitate its usage, with the portions adjacent the distal end exhibiting the most flexibility for reasons to become apparent shortly. Thus, in the exemplary embodiment where the passer is formed of high density polyethylene, the distal end is approximately 0.062 inches thick and increases in thickness to the proximal end where the thickness is approximately 0.125 inch. In that embodiment the length of the passer is approximately 18 inches. It should be pointed out at this juncture that those dimensions are merely exemplary and thus this invention contemplates passers of different sizes and shapes.

An elongated tear-drop shaped hole 232 is located in the distal end portion of the passer, with the largest portion of the hole 232A being located closely adjacent the distal end 228 and with the narrowed tail portion 232B terminating close to the midpoint of the passer. The large portion 232A of the hole 232 serves as a finger grip to facilitate the use of the device, as will be described later. The edges of the passer are smooth and rounded somewhat so that they do not push through or cut the material of the bag or pouch when the passer is introduced therein during its use. Suffice it for now to state that the passer is arranged to be held in the hand of a user adjacent its proximal end so that its distal end can be introduced through the mouth of the bag or pouch into the space between the inner surface of the bag or pouch and the outer surface of the tissue specimen or organ. To facilitate the holding of the passer by a user, the portion of the passer adjacent the proximal end includes plural 234 recesses in the edges thereof.

As can be seen in FIG. 14, the wire 224 is connected to the proximal end of the passer 222. To that end, a small hole 236 is located closely adjacent the proximal end 230 of the passer and serves as the means for connecting the passer to the wire 224. A larger hole 238 is located adjacent the small hole 236 and serves the purpose of providing a finger grip in the event it is desired to pull the passer back from within the bag from the proximal end.

The wire 224 serves as the means cutting the tissue specimen or organ to resect and remove it, as will be described in detail later. To that end the wire 224 is an elongated very flexible member having a distal end 240 and a proximal end 242. The distal end of the wire is in the form of a loop extending through the small hole 236 to fixedly secure the wire to the proximal end of the passer. The proximal end 242 of the wire is also in the form of a loop and connected to the handle 226 by means of a small opening 244 in the handle. The wire 224 is preferably a multi-strand wire with a preferred diameter of approximately 0.030 inch. However, a single strand wire can be used, if desired. The multi-strand wire is preferably since it provides a texture that helps it cut through tissue more rapidly than a single strand wire. A critical aspect of the invention is that the wire should not have sharp edges that might inadvertently cut the pouch or bag as the wire passes therethrough during the use of the device. Another advantage of multi-strand is that it is more flexible than single strand wire. Wires as small as 0.005 inch in diameter can be used. However, such small diameter wires may be susceptible to breakage. Thicker wires than the exemplary embodiment are also contemplated, e.g., wires having a diameter of up to 0.062 inch or up to 0.125 inch.

Turning now to FIGS. 14 and 16, it can be seen that the handle 226 is an elongated member that is considerably shorter in length than the passer 222. Preferably the handle is formed of the same material as the passer, e.g., high density polyethylene, is of a thickness of 0.125 inch, with a length of 8 inches. One end of the passer is in the form of an elongated hook 246. In the interest of ergonomics one side edge of the handle includes plural recesses 248 to facilitate grasping of the handle by the user.

Figure 22:
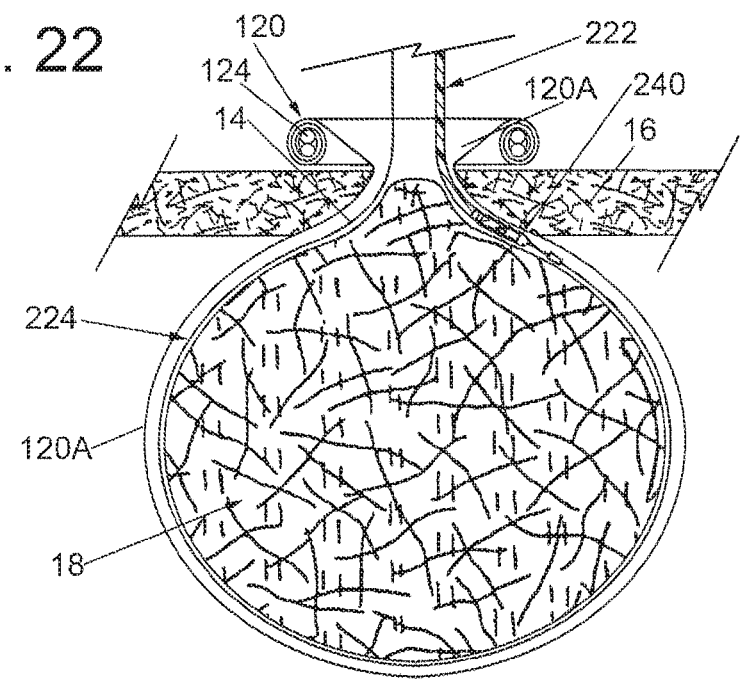
FIG. 22 is a vertical sectional view similar to FIGS. 18, 20, and 21, but showing a still further step in the use of the tissue cutter device of FIG. 14.

Use of the cutter device 220 will now be described starting with FIG. 17. As can be seen a bag or pouch 120 is disposed within an insufflated abdomen 12 of a patient with the mouth of the bag or pouch extending through a small opening 14 in the abdominal tissue 16, and with the mouth having been rolled up as described above and as shown in FIG. 13. This action exposes a portion 18A of the tissue specimen or organ 18 located within the interior of the bag or pouch so that the portion 18A is readily accessible. The user then grasps the proximal portion of the passer 222 by its finger grip recesses 234 and orients the passer so that its distal end 228 passes through the open mouth of the bag or pouch and into the space between the inner surface of the bag or pouch and the outer surface of the tissue specimen or organ 18, such as shown in FIGS. 18 and 19. The user then pushes the passer downward to cause its distal end to bend around the tissue specimen or organ and follow a path between the inner surface of the pouch or bag, such as shown in FIGS. 20 and 21. It should be noted that the flexibility of the distal end portion of the passer is such to enable it to traverse that path effectively, without buckling. Continued pushing on the passer should eventually bring the distal end portion of the passer back out through the open mouth of the bag or pouch, like shown in FIG. 22. If, however, the distal end of the passer is not able to exit the mouth of the bag or pouch, the hook 246 on the end of the handle 226 can be used to pull the distal end 228 of the passer out through the opening. That action is accomplished by introducing the hooked end 246 of the handle 226 through the open mouth of the bag or pouch and into the space between the inner surface of the bag or pouch and the outer surface of the tissue specimen or organ 18 where the distal end of the passer is located. The hook can then be extended through the hole portion 232A to grab it, whereupon pulling on the handle will pull the distal end portion of the passer out of the open mouth to the position shown in FIG. 21. Once the passer is in that position the user can pull the passer out of the bag of pouch by placing his/her finger through the hole portion 232A of the passer to pull the passer out of the pouch or bag and thereby cause the trailing wire 224 to enter the bag or pouch and follow the path of the passer like shown in FIG. 22.

Figure 24:
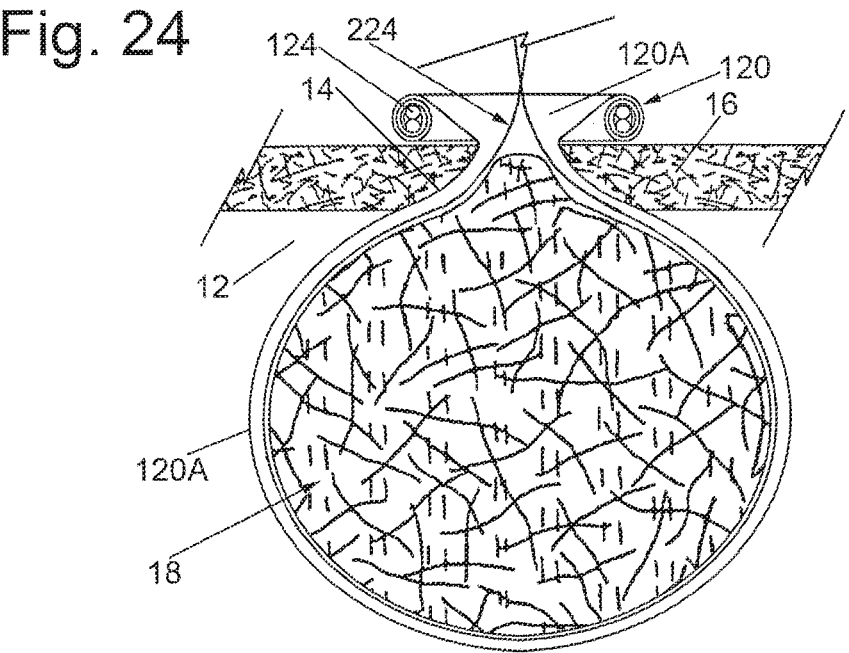
FIG. 24 is a vertical section view similar to FIGS. 18, 20, 21 and 22, but showing the step in the use of the tissue cutter device of FIG. 14 in the step illustrated in FIG. 23.
Figure 26:
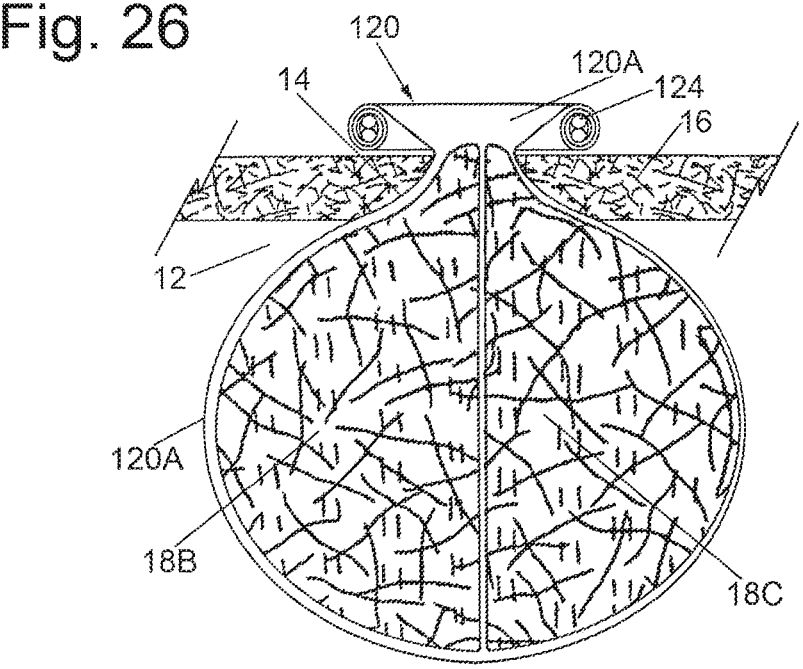
FIG. 26 is a vertical sectional view similar to FIGS. 18, 20, 21, 22, 24, and 25, but showing a still further step in the use of the tissue cutter device of FIG. 14.

Once the distal end 240 of the wire 224 is outside the mouth of the bag or pouch, such as shown in FIG. 23, the portions of the wire 224 extending out of the mouth of the bag or pouch can be crossed over as shown in that figure and in FIG. 24 to effectively encircle the tissue specimen or organ within the bag or pouch. Then the crossed-over extending portions of the wire 224 can be pulled to cause the loop of wire encircling the tissue specimen or organ to constrict, whereupon the wire cuts through the tissue specimen or organ as shown in FIG. 25. Continued pulling of the extending portions of the wire will ultimately sever the tissue specimen or organ into two sections 18B and 18C, such as shown in FIG. 26.

Figure 27:
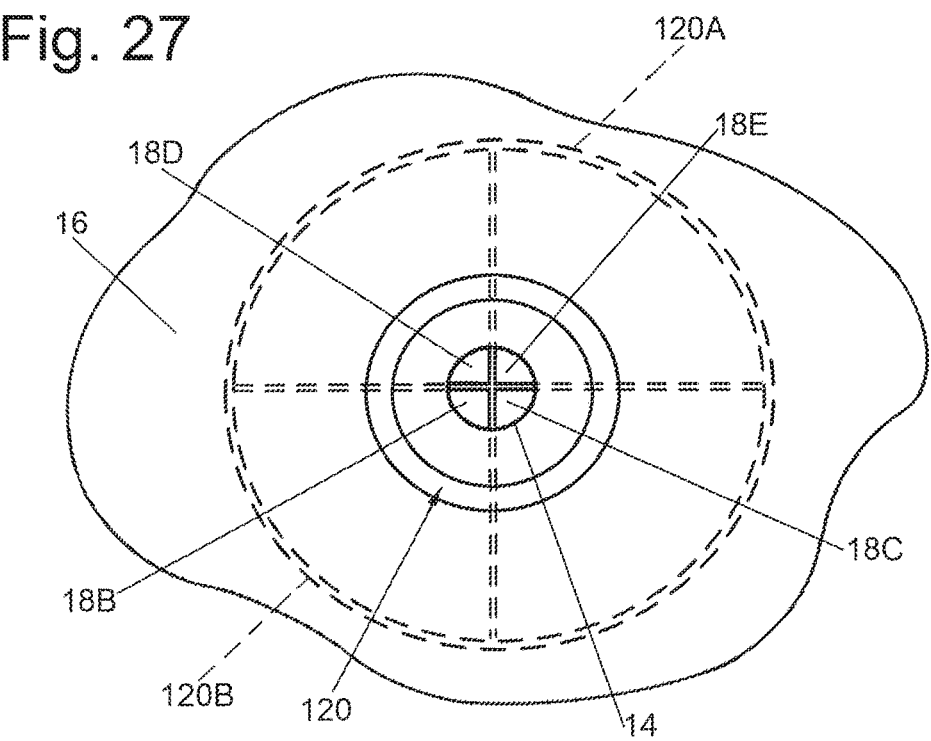
FIG. 27 is a top plan view of the abdomen of a patient wherein the tissue specimen or organ has been sectioned into four sections within a tissue specimen or organ isolating device like illustrated in FIG. 4 using the tissue cutter device of FIG. 14.

In order to facilitate the severing of the tissue it is often desirable to pull the wire 224 in a back and forth motion such that a sawing action is created. If those sections are sufficiently small, such that each can fit through the incision 14 each section can be removed through the open mouth of the bag or pouch. If however, any of those two sections is/are still too large to pass through the incision 14, the process of using the device 220 as described above can be repeated as many times as necessary. For example, FIG. 27 is a top plan view of the abdomen of a patient wherein the tissue specimen or organ has been resected into four sections 18B, 18C, 18D and 18E within a bag or pouch 120 by repeating the process twice.

In an alternative embodiment of the invention, not shown, the wire 224 is configured in such a way that once it is passed around the specimen it can be connected to a bipolar electrical generator where the electrical energy is used to further facilitate the severing of the tissue. An illustrative bipolar generator is described in EP patent publication EP2540242A1.

In FIG. 28 there is shown a portion of more preferred exemplary system 300 (FIG. 32) for cutting a tissue specimen or organ located within a pouch or bag in the body of a patient. That system is similar in many respects to the system of FIG. 23 in that it includes a tissue cutter device 320. However, it also includes a support component 350 (to be described in detail later) and a stabilizer component 380 (also to be described in detail later). The system 300 also preferably includes a bag pouch constructed in accordance with this invention, e.g., bag or pouch 120. The support 350 is used in conjunction with the passer to facilitate the insertion and transit of the passer about the tissue specimen or organ within the bag or pouch 120. The stabilizer 380 serves two purposes: First, it keeps the tissue specimen or organ 18 from rotating within the pouch or bag 120 while it is being cut. Second it holds the cutting wire sections down so that they do not inadvertently rub the bag or pouch at the opening or mouth of the bag or pouch.

The tissue cutter device 320 is basically the same construction as that of the tissue cutter device 220 of FIG. 14 except for a slight modification to the passer 322. In the interest of brevity the common features of the tissue cutter devices 220 and 320 will be given the same reference characters and the details of their construction, arrangement and function will not be reiterated. Moreover, the operation of the system 300 will not be reiterated or described except for a description of the changes to the method that are occasioned by the use of the support component 350 and the stabilizer component 380.

As will be described in detail later the support 350 is configured to be temporarily connected or coupled to the passer to form a temporary unit. That temporary unit can then be introduced into the mouth of the pouch or bag in which the tissue specimen or organ is located to facilitate the passage or transit of the passer around the tissue specimen or organ and out through the mouth of the pouch or bag to thereby carry the distal end portion of the wire so that the distal end portion of the wire is located outside the body of the patient along with the proximal end portion of that wire. The support 350 can then be removed from the passer, whereupon the wire can be used to resect the tissue specimen while the stabilizer holds the specimen to facilitate the tissue specimen's resection.

The passer 322 basically comprises a long flexible member having a distal end 228 and a proximal end 230 and is formed of the same material as passer 222. The passer includes an elongated tear-drop shaped hole 332 is located in the distal end portion of the passer, with the largest portion of the hole 332A being located closely adjacent the distal end 228 and with the narrowed tail portion 332B terminating further from the midpoint of the passer in the distal direction than does the narrowed tail portion 332B of the passer 322. The portion 332A of the hole 332 serves as a finger grip to facilitate the use of the device. A pair of proximally flaring ears 334 project outward from the opposed long side edges of the passer adjacent the tear-drop shaped slot, with each ear including a proximal edge surface 336. The surfaces 336 act as stops for engagement with respective portions of an opening (to be described later) in the support 350. Another difference between the passer 322 and the passer 222 is the fact that the passer 322 does not include the recesses 234. All other features of the passer 322 are essentially the same as the passer 222, e.g., the distal end of the cutting wire 224 is connected to the proximal end of the passer 322 and the proximal end of the wire is connected to handle 226.

The edges of the support 350, like the edges of the passer 322 are smooth and rounded somewhat so that they do not push through or cut the material of the bag or pouch after the temporary unit of the passer and support are introduced through the mouth of the bag or pouch and into the space between the inner surface of the bag or pouch and the outer surface of the tissue specimen or organ to transit the path until the distal end portion of the temporary unit is located outside of the bag or pouch.

The support 350 basically comprises a long flexible member having a somewhat rounded distal end 358 and a proximal end 360. The support is preferably formed of the same material as passer 222. A window or opening 362 is located at the distal end portion of the support 350, with the distal end of the support being split by a cut at 364. The distal end 228 of the passer is configured to be introduced into the window or opening 364 of the support 350, e.g., the distal end portions of the support contiguous with the window at the cut forming the split may open somewhat to enable the wider free (distal) end of the passer to enter the window. Once the free end of the passer is within the window the passer and support can be moved with respect to each other so that their elongated bodies are juxtaposed along and confronting each other, with the stop surfaces 336 of the passer engaging portions of the window contiguous with the proximal end of the window as best seen in FIG. 29. That action temporarily combines the two components into a temporarily combined unit, which is ready for insertion into the bag or pouch 120 holding the tissue specimen or organ, in the same manner that the passer 222 of the embodiment of FIG. 14 is introduced into that bag or pouch. The combined unit can then be pushed by the user to cause the distal end of the combined unit to bend around the tissue specimen or organ and follow a path between the inner surface of the pouch or bag, such as shown in FIG. 30. It should be noted that the flexibility of the temporarily combined unit is such to enable it to traverse that path effectively, without buckling. Continued pushing on the combined unit should eventually bring the distal end portion of the combined unit back out through the open mouth of the bag or pouch, like shown in FIG. 31.

Once the distal end of the passer 322 is located outside of the bag or pouch, the support can be removed by pulling it out via the path that it was inserted and the passer can be removed by pulling on the open end, leaving a distal end portion of the wire 224 and a proximal end portion of the wire 224 extending outside of the body of the patient, while the intermediate portion of the wire surrounds the tissue specimen or organ within the bag or pouch, in the same manner as has been described previously. The split 364 at the distal end of support 350 provides a passageway through which the distal end portion of the wire 224 that extends out of the bag or pouch can pass to enable the support 350 to be readily removed from the passer 322.

Once the distal end portion of the wire 224 is outside the mouth of the bag or pouch and the support 350 removed, the portions of the wire extending out of the mouth of the bag or pouch can be crossed over as described previously to effectively encircle the tissue specimen or organ within the bag or pouch. The cutting device 320 is then ready to cut or resect the tissue specimen or organ within the bag or pouch. To facilitate that action the system 300 of this invention makes use of the heretofore identified stabilizer 380. The stabilizer 380 is best shown in FIGS. 28 and 32, and basically comprises two generally U-shaped horizontal supports or handle portions 382A and 382B. The handle portion 382A terminates at its inward end in a pair of downwardly projecting legs 384A. In a similar manner the handle portion 382B terminates at its inward end in a pair of downwardly projecting legs 384B. The two downwardly extending legs 384A extend parallel each other and each terminates in a free end in the form of a piercing tip 386A. The two downwardly extending legs 384B extend parallel each other and each terminates in a free end in the form of a piercing tip 386B. The downwardly extending legs 384A are connected adjacent their free ends 386A by a connector or cross-bar 388A, while the downwardly extending legs 384B are connected adjacent their free ends 386B by a connector or cross-bar 388B. The handle portions 382A and 382B are located in the same plane and are interconnected to hold them in that plane by a bridging strut or link 390. The bridging strut 390 is connected to the handle portion 382A by a slide member 392A fixedly connected to one end of the bridging strut. The bridging strut 390 is connected to the handle portion 382B by a slide member 392B fixedly connected to the opposite end of the bridging strut. The slide 392A includes a passageway through which a portion of the U-shaped member forming the handle portion 382A extends. In a similar manner the slide 392B includes a passageway through which a portion of the U-shaped member forming the handle portion 382B extends. Thus, the two handle portions 382A and 382B can be either slid towards each other or away from each other to establish any desired spacing between the handle positions, and hence any desired spacing between the pairs of downwardly projecting legs 384A and 384B.

Use of the stabilizer 380 is as follows. Once the proximal end portion and the distal end portion of the wire 224 have been crossed over each other, they are pulled tight from both ends, so that the wire digs into the tissue specimen or organ, ensuring that it doesn't roll around inside the pouch or bag. The handle portions 382A and 382B of the stabilizer 380 can be spaced appropriately so that the free end portions 386A and 386B of the stabilizer are inserted through the mouth of the bag or pouch so that their piercing tips poke or burrow into the portion 18A of the tissue specimen or organ until the connectors 388 are directly in contact with the tissue portion 18A, such as shown in FIG. 32. At this time, the proximally located portion of the cutting wire 224 and the distally located portion of the cutting wire run underneath the connectors 388 as also shown in FIG. 32. As such, the connectors serve to hold the wire down during the tissue cutting procedure. In particular, one user can press on the handles of the stabilizer, while another pulls on the extending wire portions to resect the tissue specimen or organ. It should be noted at this juncture that it is preferred that the crossed over portions of the cutting wire 224 are preferably oriented so that they are above the horizontal supports or handle portions 382A and 382B. The pulling on the crossed-over extending portions of the wire causes the loop of wire encircling the tissue specimen or organ to constrict, whereupon the wire cuts through the tissue specimen or organ, while the connectors 388 hold the extending portions of the wire down so that they do not inadvertently rub the bag or pouch at the opening, which could damage the bag or pouch. Continued pulling of the extending portions of the wire by one user, while another user continues to press down or the stabilizer will ultimately sever the tissue specimen or organ into two sections like described previously. As also described earlier, in order to facilitate the severing of the tissue specimen or organ it is often desirable to pull the wire 224 in a back and forth motion such that a sawing action is created. If those resected sections of the tissue specimen or organ are sufficiently small, such that each can fit through the opening 14 each section can be removed through the open mouth of the bag or pouch. If however, any of those two sections is/are still too large to pass through the opening 14, the process of using the tissue cutting device 320 as described above can be repeated as many times as necessary.

As can be seen clearly in FIGS. 28 and 29, the support 350 includes a plurality of equidistantly located indicia 366 extending along substantially the entire length of the support 350. These indicia provide the user with a visual indication of how deep the combined passer and support are into the path about the tissue specimen or organ in the bag or pouch. While the indicia are shown as being small holes, that is merely exemplary of any type of indicia which can be used for that purpose.

Turning now to FIGS. 33-35 the details of another, and more preferred, embodiment of a stabilizer constructed in accordance with this invention will now be described. That stabilizer comprises a pair of identical stabilizer components 480. Each component 480 basically comprises a generally U-shaped horizontal support or handle portion 482 that terminates at its inward end in a pair of downwardly projecting legs 484. The downwardly extending legs 484 extend parallel each other and each terminates in a free end or piercing tip 486. The downwardly extending legs are connected adjacent their free ends by a connector or cross-bar 488. A generally curved L-shaped foot 490 is slideably mounted on the downwardly extending legs 484 below the connector or cross-bar 488.

The use of the pair of stabilizer components 480 is best understood by reference to FIGS. 34 and 35 and is as follows. Each stabilizer is adjusted such that the L-shaped foot 490 is slid to the position wherein the underside or distal surface of the foot is located immediately adjacent the piercing tip 486. The L-shaped foot of each stabilizer component 480 is placed into the mouth of the bag or pouch as shown in FIG. 34, whereupon the underside of each L-shaped foot engages a portion of the tissue specimen or organ located immediately under it. Once the L-shaped feet are in place, the handle portions 482 of the two stabilizer components 480 are pushed downward, whereupon their downwardly projecting legs slide distally with respect to their L-shaped feet such that the piercing tips 486 poke into or pierce the tissue specimen or organ as shown in FIG. 35. Each cross-bar 488 serves as a stop to prevent the associated piercing tip 486 from over-penetration of the tissue specimen or organ.

As should be appreciated by those skilled in the art, the piercing of the tissue specimen or organ by the piercing tips 486 ensures that the tissue specimen or organ is stabilized, e.g., doesn't roll around inside the pouch or bag, as the tissue specimen or organ is sectioned. That action is accomplished in a similar manner as discussed above. In particular, as shown in FIG. 35 the crossed-over proximal end portion and the distal end portion of the wire 224 are pulled tight from both ends, so that the wire digs into the tissue specimen or organ to cut or section it as described previously. The curved L-shape of each foot 490 helps to hold its associated stabilizer 480 in place during the tissue cutting or sectioning since it curves under the patient's abdominal wall. Moreover, each foot also serves to protect the bag or pouch from damage by the cutting wire 224, since it is interposed between the cutting wire and the bag as clearly shown in FIG. 35.

In FIGS. 36-41 there is shown another and most preferred exemplary embodiment of a tissue specimen or organ isolating device 500 (FIG. 41) constructed in accordance with this invention for facilitating the removal of a large organ or tissue specimen from within a space, e.g., the peritoneal cavity, in the body of a patient via an opening to that space. The components making up the device 500 are shown in FIGS. 36-40. In particular, the device 500 basically comprises a bag or pouch 520 shown in FIG. 36, a support ring assembly 522 shown in FIG. 39, and a split ring 524 shown in FIG. 40. As mentioned previously the opening into the body of the patient may be an incision or natural body opening, such as the vagina, and may be smaller than the organ/tissue specimen to be removed. As will be described in detail later, the support ring assembly 522 is made up of a resilient material ring and a section of heat shrinkable tubing to secure the ends of the ring together. The split ring 524 is made up of a plurality of split ring sections which are arranged to be connected together. In the exemplary embodiment the split ring is composed of two sections 524A and 524B and plural connectors to connect the sections to each other, all of which will also be described later.

As can be seen in FIGS. 36, 37, and 41 the bag or pouch 520 is in the form of a hollow structure formed by a pair of panels 520A and 520B. Each panel is formed of a sheet or web of a thin flexible material, e.g., polyurethane film that is 0.008 inches thick. Both panels are of a generally U-shape and of the same size as the other panel, with the panels being superimposed on each other. In the exemplary embodiment shown each panel has a pair of long, linear side edges 526 and an arcuate, e.g., semi-circular bottom edge 528. The panels 520A and 520B are connected together along a heat seal line 534 extending close and parallel to the adjacent peripheral edges of the panels form a hollow interior cavity 520C (FIG. 41) within the bag or pouch. The two ends of the seal line 134 terminate at respective top edge portions 530. Each panel 502A and 520B includes a portion 532 which projects outward from the top edge portions 530. As best seen in FIG. 37, the outwardly projecting portion 532 of the panel 520A is folded down into engagement with the outer surface of the panel 520A and is sealed thereto by two transverse heat seal lines. In particular, the folded over portion 532 of the panel 520A is sealed to the outer surface of that panel by a first transverse linear seal line 536A and a second transverse seal line 538A. In a similar manner the outwardly projecting portion 532 of the panel 520B is folded down into engagement with the outer surface of the panel 520B and is sealed thereto by a first transverse heat seal line 536B and a second transverse seal line 538B. The seal lines 536A, 538A, 538A and 538B are preferably formed by a thermal or heat seal bond, but can be formed by any suitable means, e.g., an adhesive bond, etc. The top of the folded over portion 532 of the panel 520A forms the top edge 540 of that panel and is contiguous with the top edge portions 530 of that panel. In a similar manner the top edge of the folded over portion 532 of the panel 520B forms the top edge of that panel and is contiguous with the top edge portions 530 of that panel.

As best seen in FIG. 41, the two panels 520A and 520B are not secured together at their top edges to form the mouth 548 of the bag or pouch. It is through the mouth that the excised tissue specimen 18 or organ is placed for location within the bag or pouch and through that mouth that severed portions of the tissue specimen or organ are removed, as will be described later.

The folded over portion 532 of the panel 520A which is located between the top edge 540 and the transverse seal line 536A forms a narrow transversely extending passageway or channel 542A. The channel 542A is open at each end. In a similar manner the folded over portion 532 of the panel 520B which is located between the top edge 540 and the transverse seal line 536B forms a narrow transversely extending passageway or channel 542B. The channel 542B is open at each end. The channel 542A is configured for receipt of one portion of the support ring 522, while the channel 542B is configured for receipt of the remaining portion of the support ring 522. The placement of the support ring 522 within the narrow channels 542A and 542B will be described later.

The portion 532 of the panel 520A which is located between the transverse seal line 536A and the transverse seal line 538A forms a wide transversely extending passageway or channel 544A. The channel 544A is open at each end. In a similar manner the folded over portion 532 of the panel 520B which is located between the transverse seal line 536B and the transverse seal line 538B forms a wide transversely extending passageway or channel 544B. The channel 544B is open at each end. The channel 544A is configured for receipt of one portion of the split ring section 524A, while the channel 544B is configured for receipt of the split ring section 524B. The placement of the split ring sections 524A and 524B within the wide channels 544A and 544B, respectively, will be described later. Suffice it for now to state that the portions of the folded over portion 532 at each end of the channel 544A is in the form of a tab or flap 546A (FIGS. 36 and 41), which can be grasped by a user to open either end of the channel 544A. In a similar manner the folded over portion 532 at each end of the channel 544B is in the form of a tab or flap (not shown, but like the like the tab or flap 546A) and which can be grasped by a user to open either end of the channel 544B.

In accordance with one preferred aspect of this invention bag or pouch 520 incudes means for identifying whether a user of the bag or pouch is looking at the bag or pouch via a laparoscope or other similar viewing instrument from outside of the bag or pouch or from inside of it. Thus, in the exemplary embodiment shown in FIG. 36, the transverse seal lines 536A and 536B include direction-marking indicia 550 which when viewed from inside of the bag or pouch by a viewing instrument, e.g., a laparoscope 10, will alert the viewer that the viewing instrument is directed into the bag or pouch. In the exemplary embodiment the indicia 550 constitutes the words "PHOENIX" and "INSIDE" which are embossed into the material making up the bag or pouch during the formation of the heat seals 536A, 536B, 538A and 538B. Those words repeatedly alternate along the length of each of the transverse seal lines. Thus when viewed from the outside of the bag the alternately repeating words "PHOENIX" and "INSIDE" making up the indicia 550 appear as a mirror or reversed image. This feature enables personnel viewing the procedure via a conventional laparoscope to know whether the image produced by the scope is from the outside of the bag or pouch or from inside the bag or pouch. This is particularly important since conventional laparoscopes have a very narrow angle of view and relatively high magnification, making navigation and a determination of a viewing direction somewhat difficult.

The support ring 522 is best seen in FIGS. 38 and 39 and basically comprises an elongated flexible and somewhat resilient member. One preferred exemplary embodiment of the support ring is formed of a ring-like section of nitinol wire with hooks 522A and 522B formed at respective ends of the nitinol wire. The two hooks at the ends of the wire are configured to be attached to each other to form a ring, with the two hook ends being held together by a section of heat shrinkable tubing 522. In particular, during the assembly process of the support ring an unshrunk section of heat shrinkable tubing 552 is slid over one hook of the nitinol wire making up the support ring so that it is in place on that wire. The two hooks 522A and 522b are then connected to each other and the unshrunk heat shrinkable tubing is then slid over the interconnected hooks. Heat is then applied to the heat shrinkable tubing to cause it to shrink about the interconnected hooks, thereby locking them together and completing the support ring as shown in FIG. 39. Being flexible and somewhat resilient, the support ring 522 is configured to be collapsed or flattened to facilitate the introduction of the bag or pouch 520 into the patient, as will be described later.

Turning now to FIGS. 40 and 41, the details of the split ring 524 will now be described. In the exemplary embodiment shown in FIGS. 40 and 41 the split ring 524 is made up of plural, e.g., two, elongated flexible split ring sections 524A and 524B which are arranged to be extended through the channels 544A and 544B in panels 520A and 520B, respectively, and thereafter connected together to form the split ring 524 and to connect that split ring to the bag or pouch 520. It should be pointed out at this juncture that the split ring 524 need not be made up of two spit ring sections, but can be made up of a single split ring sections or more than two split ring sections. For example, if the split ring is made up of only a single split ring section, that section may be constructed like either the split ring sections 524A or 524B, but double the length thereof, and with a pair of ends configured to be connected to each other.

The assembly of the split ring and its connection to the bag or pouch is accomplished during the process of using the bag or pouch and will be described later. Suffice for now to state that after the tissue specimen or organ has been disposed within the bag or pouch within the patient's insufflated peritoneal space, the mouth 548 of the bag or pouch is withdrawn through the incision 14 from the peritoneal space so that it is outside the body of the patient, i.e., is externalized as described earlier. The split ring sections 524A and 524B are extended through the channels 544A and 544B in the panels 520A and 520B, respectively, so that they can be connected together. The sections 524A and 524B are identical in construction and each comprises a three lumen tube, e.g., polyurethane tubing with a durometer in the 80-90 Shore A range, with each lumen of the tube having an inside diameter of 0.25 inches and an outside diameter of 0.375 inches. In order to effect the connection of the two split ring sections 524A and 524B together to form the split ring 524 four threaded rod-like connectors 554 are provided. Two rod-like connectors are provided for each split ring section. Both of those two rod-like connectors can be located on the same end of the split ring sections, like shown in FIG. 40, or one rod-like connector may be provided in one open end of one of the lumens of that split ring section and the other rod-like connector of that split ring section may be provided in the open end of another of those lumens at the opposite end of the split ring section. While it is contemplated that the two split-ring sections 524A and 524B are connected by two pairs of rod-like connector 544, as just described. That is merely exemplary. Thus, the split ring sections can be connected together by at least one rod-like connector at each end of the split ring section. In any case, the two split ring sections 524A and 524B can be connected various ways. For example, they can be connected as shown in FIG. 40 wherein the three lumens of two sections are oriented parallel to each other so both ends of one lumen are located above both ends of the other lumen. Alternatively, they may be twisted similarly to that shown in FIG. 11 wherein the upper and lower of the three lumens are twisted 180 degrees to facilitate the rolling up of the pouch as discussed above, if such action is desired.

The tissue specimen or organ isolating device 500 can be used as follows. After the organ or tissue specimen 18 has been excised within the peritoneal space via laparoscopic instruments so that it is free within the peritoneal space the lower end the bag or pouch 520 (i.e., the end opposite the mouth 548) is folded or rolled up to collapse the bag or pouch and the support ring 522 into a compact or narrow structure for easy introduction through the incision 14 into the insufflated peritoneal space 12. Once the bag or pouch and the support ring have been collapsed, with the mouth 548 of the bag or pouch directed upward, the collapsed bag or pouch and its support ring can be inserted through the incision 14 into the patient's peritoneal space. To that end, the trocar that had been extended through the incision is removed, and the collapsed bag or pouch and its support ring are extended through the incision so that the bag or pouch and its support ring are fully within the peritoneal space. Alternatively, the bag or pouch and it support ring can be inserted into the peritoneal space through the trocar without removal of the trocar from the patient. This may be done in order to better maintain pneumoperitoneum during insertion. In either case, inasmuch as the support ring 522 is resilient it will tend to spring back to its normal, e.g., approximately circular, ring-like configuration, thereby opening the mouth of the bag or pouch when it is free of the incision or trocar, as the case may be.

Once the bag or pouch 520 is in place within the peritoneal space 12, the trocar (not shown) can be reinserted into the peritoneal space via the incision. A grasper instrument of any suitable type (not shown) can then be inserted through the trocar extending through the incision through which the bag or pouch was inserted and additional graspers (not shown) can be extended through other trocars (not shown) into the peritoneal space. These graspers can be used to grasp the bag or pouch 120 to ensure that the mouth of the bag or pouch is open and to pull the open mouth of the bag or pouch to a desired position with respect to the excised organ or specimen 18 to be removed. Thus, for example, the grasper that is extended through trocar in the incision into which the bag pouch was inserted can be used to hold the bag or pouch with the open mouth at a desired position and a second grasper extending through another trocar can be used to move the excised tissue specimen or organ into and through the mouth of the bag or pouch, while holding the bag or pouch in place with the first grasper. This action is preferably accomplished by viewing it through a viewing instrument, e.g., a conventional laparoscope. Inasmuch as the angle of view of a laparoscope is quite narrow and the image presented on the associated monitor is greatly magnified, it is sometime difficult to determine the whether the laparoscope is viewing the procedure from outside the bag or pouch or from inside the bag or pouch. The inclusion of the direction-bearing indicia 550 in the bag or pouch enables the viewer to readily determine the direction of view. In this connection if the words "PHOENIX INSIDE" appear normal (unreversed) the viewer will know that the laparoscope is directed into the interior of the bag or pouch, like shown by the laparoscope 10A in FIG. 41. If however, the letters making up those words appear reversed, that will designate that the laparoscope is directed toward the exterior of the bag or pouch, like shown by the laparoscope 10B shown in FIG. 41. Thus, the user can be quite efficient in manipulating the instruments to excise the tissue specimen or organ and move it through the open mouth of the bag or pouch into the interior of the bag or pouch.

Once the tissue specimen or organ 18 is within the bag or pouch 120, the incision 14 into which the bag or pouch was inserted can be enlarged by use of a scalpel if necessary. The trocar extending through the incision into which the bag or pouch had been inserted can then be withdrawn along with the grasper extending therethrough to pull a portion of the mouth of the bag or pouch through the incision so that it is located outside of the patient's abdomen, whereupon the mouth of the bag or pouch 520 is externalized, as described earlier. Once the mouth of the bag or pouch is externalized, the resilient nature of the support ring 522 will cause the mouth of the bag or pouch to spring open. At that point the bag or pouch is ready to have the spit ring 524 mounted thereon. To that end, one end of the split ring section 524A is inserted into one end of the channel 544A of the panel 520A. The split ring is slid down that channel until the end of the split ring exits the opposite end of that channel. The other split ring 524B is inserted into one end of the channel 544B in the other panel 520B and extended therethrough until it exits the opposite end of that channel. The two ends of the spit ring sections 524A and 524B are then connected together using the threaded rod-like connectors 554. If the split ring is made up of only one split ring section, one end of that single split ring section is inserted into one end of the channel 544A of the panel 520A. The split ring is slid down that channel until the end of the split ring exits the opposite end of that channel, from whence it is introduced into the adjacent end of the channel 544B, whereupon it is extended through that channel until it exits the opposite end of that channel. The two ends of the single spit ring section are then connected together using at least one, and preferably two of the threaded rod-like connectors 554.

Once the spit ring 524 has been assembled and in place, it is ready to have the bag or pouch 520 rolled up about it and the support ring 522. To that end, the split ring 524 is flipped or rotated inward, thus rolling it up. That rolling or flipping action is repeated, with each inversion of the split ring causing a portion of the bag or pouch to be wrapped around it and the support ring. This serves the purposes of pulling the tissue specimen or organ 18 into the incision 14 and applying tension to the incision such that a portion of the organ or tissue specimen will be located within the rolled-up portion of the pouch outside of the patient's body, in a manner like shown in FIG. 13. At that point the surgeon can cut off pieces of the tissue specimen or organ using forceps and scalpel. Alternatively, the tissue specimen or organ 18 can be removed using the systems as described above with reference to FIGS. 17-35.

Once the organ or specimen has been cut away and removed, the extending portion of the bag or pouch 520 can be grasped to remove it from the incision 14, thereby carrying with it any residual portions of the organ or tissue specimen, e.g., cells, etc. that had not been removed. After the bag or pouch 520 has been removed from the patient, the incision 14 is ready for closure.

As should be appreciated by those skilled in the art from the foregoing, by using systems and methods in accordance with this invention an organ or tissue specimen can be removed from the patient via an incision or body opening that is smaller than the organ/tissue specimen. This is obviously advantageous to the patient since he/she needn't have to endure having a large incision.

It should be pointed out at this juncture that the systems and methods of use as described above are merely exemplary and thus other systems/devices can be constructed in accordance with the teaching of this invention and other methods of removing an organ or tissue specimen from the body of a patient through an incision or natural body opening can be accomplished, as well. For example, the direction-marking indicia for providing a viewer using a laparoscope or other similar viewing instrument with a means to determine the direction being viewed, need not be the particular words used in the above example. In fact, the indicia need not be words, but can be any symbol, color, etc., which when viewed from inside the bag or pouch appears different than when viewed from outside the bag or pouch. Moreover, such indicia need not be formed by means of embossing, but can be formed in various ways, e.g., printing, etc.

Without further elaboration the foregoing will so fully illustrate our invention that others may, by applying current or future knowledge, adopt the same for use under various conditions of service.

We claim:

1. A device for use with at least one viewing instrument for facilitating the removal of an organ or tissue specimen from the body of a patient through an opening in the patient's body, the organ or tissue specimen being located within an interior space in the patient adjacent the opening, said device being configured for insertion through the opening into the interior space so that it is entirely within the interior space without any portion extending through the opening, said device comprising:

a bag or pouch having an interior cavity and being formed of a thin and flexible sidewall terminating in an open top forming a single mouth in communication with said interior cavity, said bag or pouch being configured to be collapsed for introduction through the opening into the interior space without any portion of said bag extending through the opening;

a support ring located adjacent said single mouth and configured to be collapsed by squeezing it to close said single mouth, said support ring comprising a ring-like member having a pair of ends configured to be connected together to form said support ring, said flexible sidewall of said bag or pouch also being configured to be collapsed to assume a compact state immediately adjacent said support ring to form a collapsed device configured to be inserted through the opening in the patient's body into said interior space and free of the opening, whereupon said single mouth of said bag or pouch springs open and said entire device is located within the interior space and is freely moveable in the interior space without any portion of said device being located outside the interior space, whereupon the organ or tissue specimen can be introduced into said interior cavity through said open single mouth;

direction-bearing indicia on said bag or pouch, said direction-bearing indicia being configured when viewed by the at least one viewing instrument from inside said interior cavity to appear in one condition and when viewed by the at least one viewing instrument from outside said interior cavity to appear in another condition, said other condition being visually different than said one condition, whereupon a user of said device can readily determine whether the device is being viewed by the at least one viewing instrument from inside said interior cavity or outside said interior cavity to facilitate the introduction of the organ or tissue specimen into said interior cavity through said open single mouth, said open single mouth being configured to be drawn through said opening to a position outside of the body of the patient after the organ or tissue specimen has been introduced into said interior cavity; and at least one split ring section having a pair of ends, said at least one split ring section being configured for location within a passageway in said bag or pouch adjacent said open single mouth when said open single mouth is outside of the body of the patient, whereupon said pair of ends of said at least one split ring section can be connected together to form a continuous ring having sufficient strength to enable said sidewall to be rolled up about said support ring and said continuous ring.

2. The device of claim 1 wherein said support ring is configured to automatically expand to a non-collapsed state opening said single mouth when said bag or pouch is located within the interior space in the patient.

3. The device of claim 2 wherein said support ring is formed of nitinol wire and wherein, each of said ends of said support ring is in the form of a connector, said connectors being configured to connect to one another to form said support ring.

4. The device of claim 3 additionally comprising a section of heat shrinkable tubing configured for locking said connectors together once they have been connected.

5. A device for use with at least one viewing instrument for facilitating the removal of an organ or tissue specimen from the body of a patient through an opening in the patient's body, the organ or tissue specimen being located within an interior space in the patient adjacent the opening, said device being configured for insertion into the interior space, said device comprising:

a bag or pouch having an interior cavity and being formed of a thin and flexible sidewall terminating in an open top forming a single mouth in communication with said interior cavity, said bag or pouch being configured to be collapsed for introduction through the opening into the interior space;

a support ring located adjacent said single mouth and configured to be collapsed by squeezing it to close said single mouth, said support ring comprising a ring-like member having a pair of ends configured to be connected together to form said support ring, whereupon said device is collapsed so that it can be inserted through the opening in the patient's body into said interior space and free of the opening, said support ring being configured to cause said single mouth of said bag or pouch to spring open when and device is located within the interior space, whereupon the organ or tissue specimen can be introduced into said interior cavity through said open single mouth;

direction-bearing indicia on said bag or pouch, said direction-bearing indicia being configured when viewed by the at least one viewing instrument from inside said interior cavity to appear in one condition and when viewed by the at least one viewing instrument from outside said interior cavity to appear in another condition, said other condition being visually different than said one condition, whereupon a user of said device can readily determine whether the device is being viewed by the at least one viewing instrument from inside said interior cavity or outside said interior cavity to facilitate the introduction of the organ or tissue specimen into said interior cavity through said single mouth, said single mouth being configured to be drawn through said opening to a position outside of the body of the patient after the organ or tissue specimen has been introduced into said interior cavity; and at least one split ring section, said bag or pouch having a passageway adjacent said open single mouth and being configured to mount said at least one split ring section therein and adjacent said support ring, said at least one split ring section comprising a pair of ends configured to be connected together to form a continuous ring after said open single mouth is outside of the body of the patient to form a continuous ring having sufficient strength to enable said sidewall to be rolled up about said support ring and said continuous ring.

6. The device of claim 5 wherein said sidewall of said bag or pouch comprises a pair of superimposed panels formed of a flexible material and which are connected together along portions of the periphery thereof to form said interior cavity, each of said pair of superimposed panels including an outer surface and a top portion which is folded over said outer surface to from a top edge of said panel, said top portion being sealed to said outer surface of said panel by a first transverse seal line to form a first passageway or channel located between said top edge and said first transverse seal line, said top portion of said panel being sealed to said outer surface of said panel by a second transverse seal line to form a second passageway or channel located between said first transverse seal line and said second transverse seal line, said first passageway or channel being configured to receive a portion of said support ring therein, said second passageway or channel being configured to receive one of said split ring sections therein.

7. The device of claim 6 wherein said direction-bearing indicia are formed at least one of said first and second transverse seal lines.

8. The device of claim 7 wherein said first and second transverse seal lines are heat seal lines and wherein said indicia is embossed in said heat seal lines.

9. The device of claim 5 wherein said at least one split ring section comprises at least one connector for connecting said pair of ends of said at least one split ring section together.

10. The device of claim 9 wherein said at least one split ring section comprises plural lumens extending side-by-side along each other.

11. A method of removing a tissue specimen or organ from the body of a patient through an opening in the patient's body, the organ or tissue specimen being located within an interior space in the patient's body adjacent the opening, said method comprising:

providing a tissue specimen or organ isolating device comprising a flexible bag or pouch having an interior cavity, an open top forming a single mouth in communication with said interior cavity, a first ring located adjacent said mouth, and direction-bearing indicia on said bag or pouch, said first ring being a collapsible support ring, said direction bearing indicia being configured when viewed by a viewing instrument from inside said interior cavity to appear in one condition and when viewed by a viewing instrument from outside said interior cavity to appear in another condition, said other condition being visually different than said one condition, whereupon a user of said device can readily determine whether the device is being viewed by the at least one viewing instrument from inside said interior cavity or outside said interior cavity;

squeezing said device to collapse said support ring to close said single mouth and thereby cause said device to be in a compact state;

inserting said collapsed device through the opening in the patient's body into the interior space, whereupon said device is entirely within the interior space and freely moveable in the interior space and without any portion of said device being located outside the interior space;

causing said single mouth of said device to open when said device is within the interior space;

causing an excised tissue specimen or organ to be introduced through said open single mouth so that said excised tissue specimen or organ is located within said interior cavity;

utilizing a viewing instrument inserted into the interior space so that a user of said tissue specimen or organ isolating device can view said direction-bearing indicia to determine if said bag or pouch is being viewed by said viewing instrument from inside said interior cavity of said bag or pouch or outside said bag or pouch to facilitate the introduction of the organ or tissue specimen into said interior cavity through said open single mouth;

collapsing said open single mouth of said device after the excised tissue specimen or organ is located in said interior cavity;

withdrawing said collapsed single mouth of said device out of the opening in the patient's body;

causing said collapsed single mouth of said device to open into a ring-like state outside the patient's body; and inserting at least one split ring section having a pair of ends within a passageway in said bag or pouch adjacent said single mouth when said single mouth is in said ring-like state outside the patient's body;

connecting said pair of ends together to form a continuous ring; and rolling up said bag or pouch around said continuous ring to bring the excised tissue specimen or organ close to the opening in the patient's body where it can be seen from outside of the patient's body.

12. The method of claim 11, wherein said collapsible support ring automatically opens said single mouth of said device when said device is located in the interior space.

13. The method of claim 11, additionally comprising removing said excised tissue specimen or organ from the patient's body through said single mouth of said bag or pouch.

14. The method of claim 13, additionally comprising removing said bag or pouch from the patient's body via the opening in the patient's body.

15. The method of claim 13, additionally comprising resecting portions of the excised tissue specimen or organ from other portions thereof and removing the resected portions of the excised tissue specimen or organ from the patient's body via the opening in the patient's body.

* * * * *